(12) United States Patent
Barnacka et al.

(10) Patent No.: US 11,992,360 B2
(45) Date of Patent: May 28, 2024

(54) SYSTEM AND METHOD FOR HEART RHYTHM DETECTION AND REPORTING

(71) Applicants: Anna Barnacka, Cambridge, MA (US); Charles R Bridges, Auburndale, MA (US); Karlen Shahinyan, Boston, MA (US)

(72) Inventors: Anna Barnacka, Cambridge, MA (US); Charles R Bridges, Auburndale, MA (US); Karlen Shahinyan, Boston, MA (US)

(*) Notice: Subject to any disclaimer, the term of this patent is extended or adjusted under 35 U.S.C. 154(b) by 831 days.

(21) Appl. No.: 16/932,683

(22) Filed: Jul. 17, 2020

(65) Prior Publication Data
US 2021/0015442 A1 Jan. 21, 2021

Related U.S. Application Data

(60) Provisional application No. 62/876,341, filed on Jul. 19, 2019.

(51) Int. Cl.
*A61B 5/00* (2006.01)
*A61B 5/021* (2006.01)
(Continued)

(52) U.S. Cl.
CPC ............ *A61B 7/04* (2013.01); *A61B 5/02108* (2013.01); *A61B 5/6817* (2013.01);
(Continued)

(58) Field of Classification Search
CPC .. A61N 1/36031; A61N 1/3702; A61N 1/365; A61N 1/36036; A61N 1/395;
(Continued)

(56) References Cited

U.S. PATENT DOCUMENTS

2011/0213263 A1 9/2011 Haartsen et al.
2015/0109124 A1 4/2015 He et al.
(Continued)

FOREIGN PATENT DOCUMENTS

EP 3010249 A1 4/2016
WO PCT/US2019/017832 8/2019

OTHER PUBLICATIONS

Neuman, M. R. (2000, Biopotential Electrodes, J.D. Bronzino Ed., Second Edition, CRC Press LLC, Boca Raton) (Year: 2000).*
(Continued)

*Primary Examiner* — Deborah L Malamud
(74) *Attorney, Agent, or Firm* — John Gillis

(57) ABSTRACT

A system and method for heart rhythm detection and reporting are disclosed. This cardiology system includes a biosensor system and a data analysis system. The biosensor system is worn by an individual and includes sensors that detect biosignals including infrasonic signals from the individual. The data analysis system receives the biosignals from the biosensor system, and determines heart rhythms of the individual based upon the biosignals. The system identifies at least some of biosignals as being associated with cardiovascular activity, such as pulse wave signals. Preferably, the biosensor system is an in-ear biosensor system that detects the biosignals via left and right earbuds placed within or at ear canals of the individual. The system can also identify arrhythmias including atrial fibrillation (Afib) arrhythmias from the heart rhythms, report information to health care and safety professionals and update medical records of the individuals.

31 Claims, 26 Drawing Sheets

(51) Int. Cl.
 *A61B 7/04* (2006.01)
 *A61B 8/06* (2006.01)
(52) U.S. Cl.
 CPC .......... *A61B 5/6833* (2013.01); *A61B 5/7207* (2013.01); *A61B 5/747* (2013.01); *A61B 8/065* (2013.01); *A61B 2562/0247* (2013.01)
(58) Field of Classification Search
 CPC .. A61N 1/36128; A61N 1/00; A61N 1/36528; A61N 1/36038; A61N 1/36164; A61N 1/3628; A61B 5/4836; A61B 5/7264; A61B 5/024; A61B 7/00; A61B 5/24; A61B 5/486; A61B 5/375; A61B 2562/0204; A61B 5/02; A61B 5/377; A61B 5/6801; A61B 5/02108; A61B 5/0004; A61B 5/38; A61B 8/00; A61B 8/02; A61B 8/04; A61B 8/06; A61B 8/065; A61B 8/0883; A61B 8/46; A61B 2034/2063; Y10S 706/924; Y10S 128/92; Y10S 128/923; Y10S 128/901; Y10T 29/49169; Y10T 29/49826; Y10T 436/143333; Y10T 29/49002; Y10T 29/49004; Y10T 29/49147; Y10T 29/53661; Y10T 436/14; Y10T 436/147777; Y10T 436/17; Y10T 436/18
 See application file for complete search history.

(56) References Cited

U.S. PATENT DOCUMENTS

| | | | |
|---|---|---|---|
| 2016/0361041 A1* | 12/2016 | Barsimantov | A61B 8/065 |
| 2017/0135896 A1 | 5/2017 | Snow | |
| 2019/0022348 A1 | 1/2019 | Read et al. | |
| 2019/0133548 A1* | 5/2019 | Cai | A61B 5/318 |
| 2019/0247010 A1 | 8/2019 | Barnacka et al. | |

OTHER PUBLICATIONS

International Search Report and Written Opinion, dated Oct. 28, 2020, from related International Application No. PCT/US2020/042684, filed on Jul. 17, 2020. 7 pages.

EPO Communication with mail date Jul. 7, 2023, for counterpart application EP 20844608.8 filed Jan. 20, 2022, announcing first Office Action. Sent to Attorney by European foreign associate on Jul. 28, 2023.

European Search Opinion with dated Jul. 7, 2023, for counterpart application EP 20844608.8 filed Jan. 20, 2022. Sent to Attorney by European foreign associate on Jul. 28, 2023.

Supplemental European Search report with dated Jun. 23, 2023, for counterpart application EP 20844608.8 filed Jan. 20, 2022. Sent to Attorney by European foreign associate on Jul. 28, 2023.

* cited by examiner

| medical record 50 |
|---|
| user data (e.g. name, address, telephone) 902 |
| biometric data (e.g. age, weight, height) 904 |
| insurance data 906 |
| baseline heart rhythm 920 |
| derived heart rhythm 922 |

FIG. 2B

| user account 60 |
|---|
| credentials (e.g. user/password, biometric ID) 907 |
| biosensor system version 962 |
| cardiovascular user application (user app) version 964 |

FIG. 2C

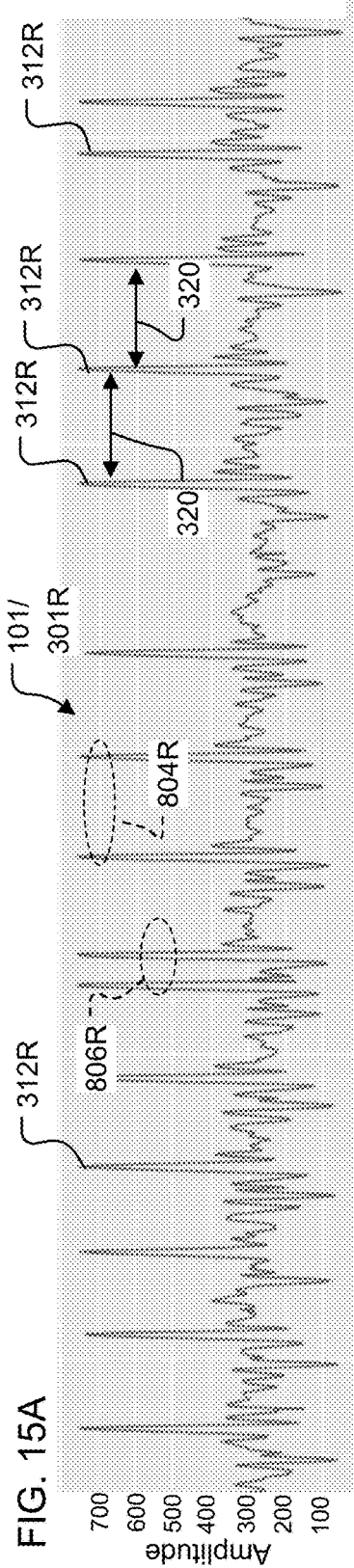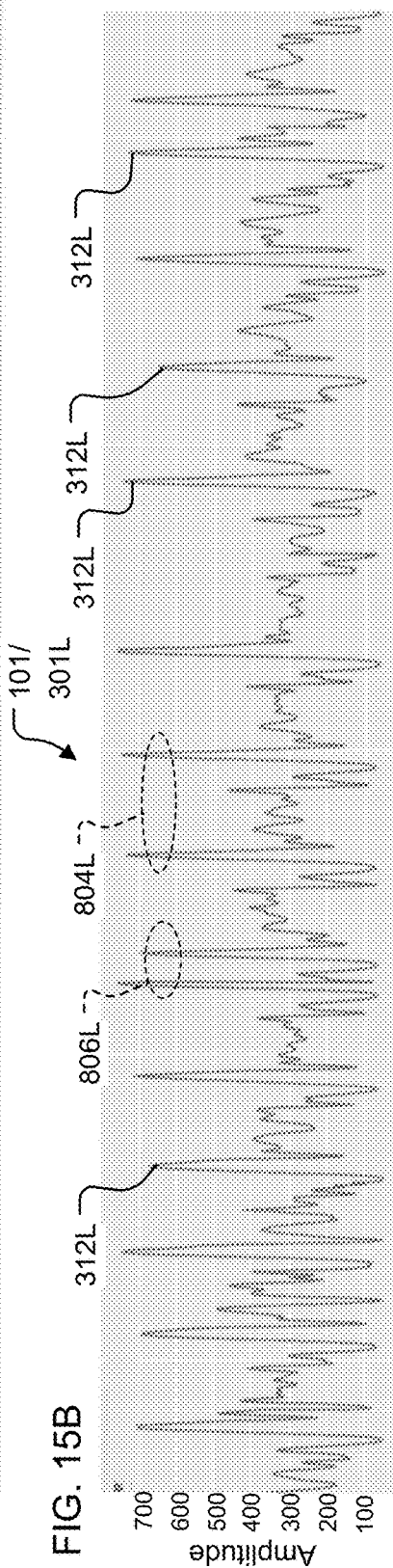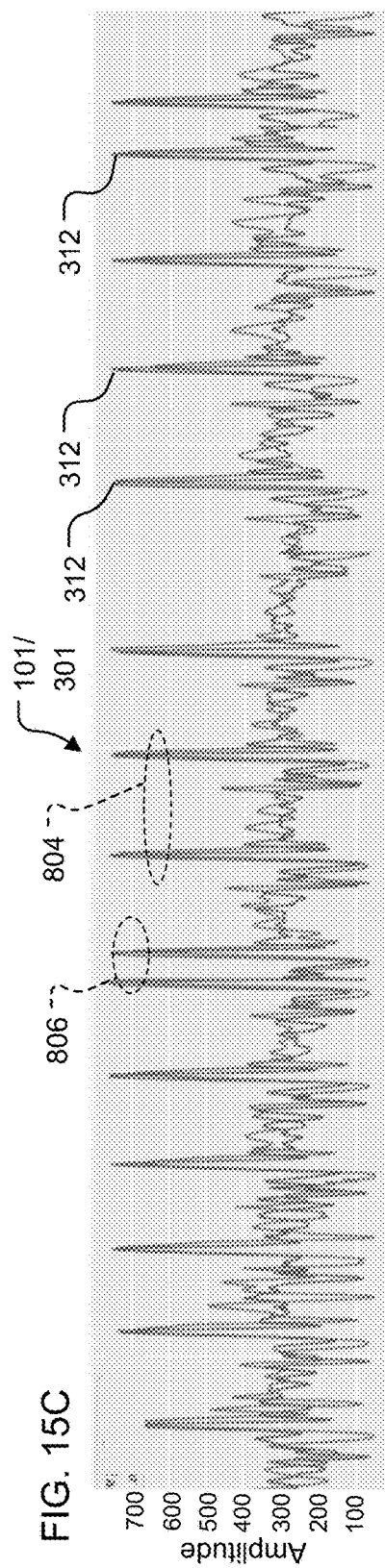

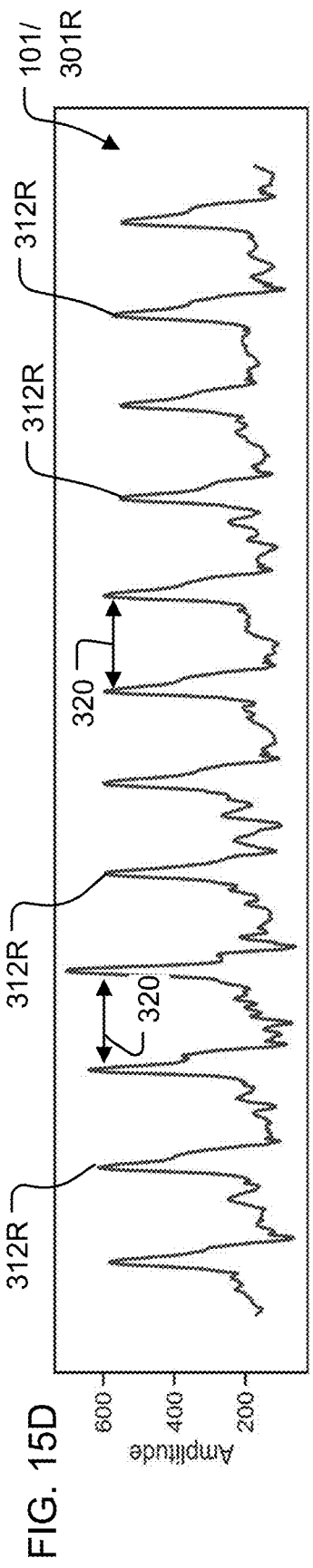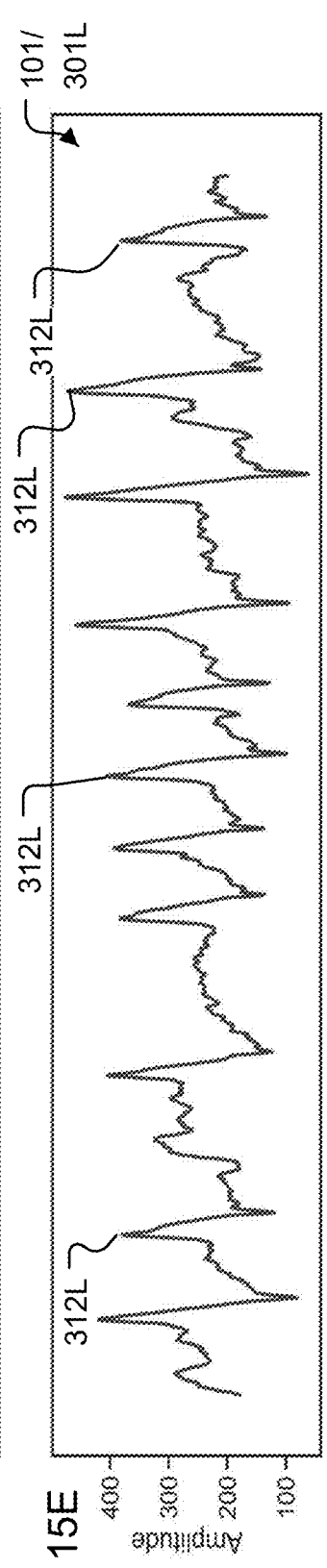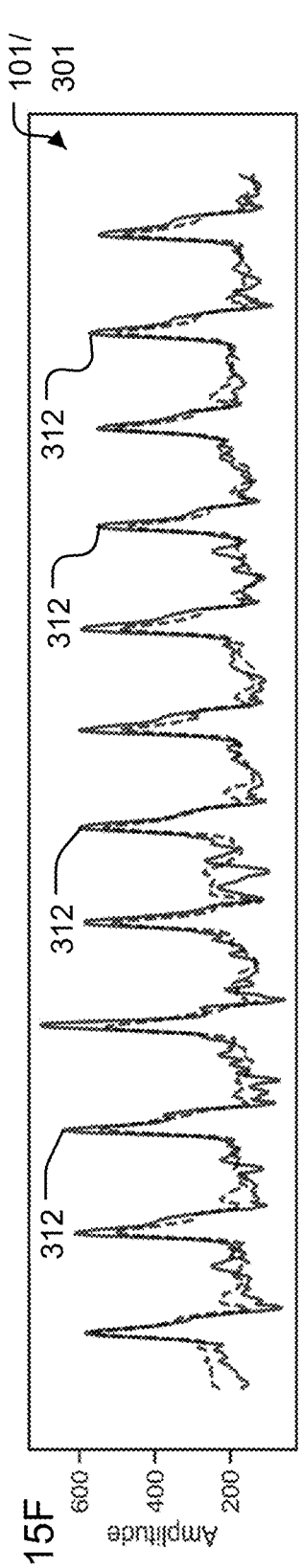

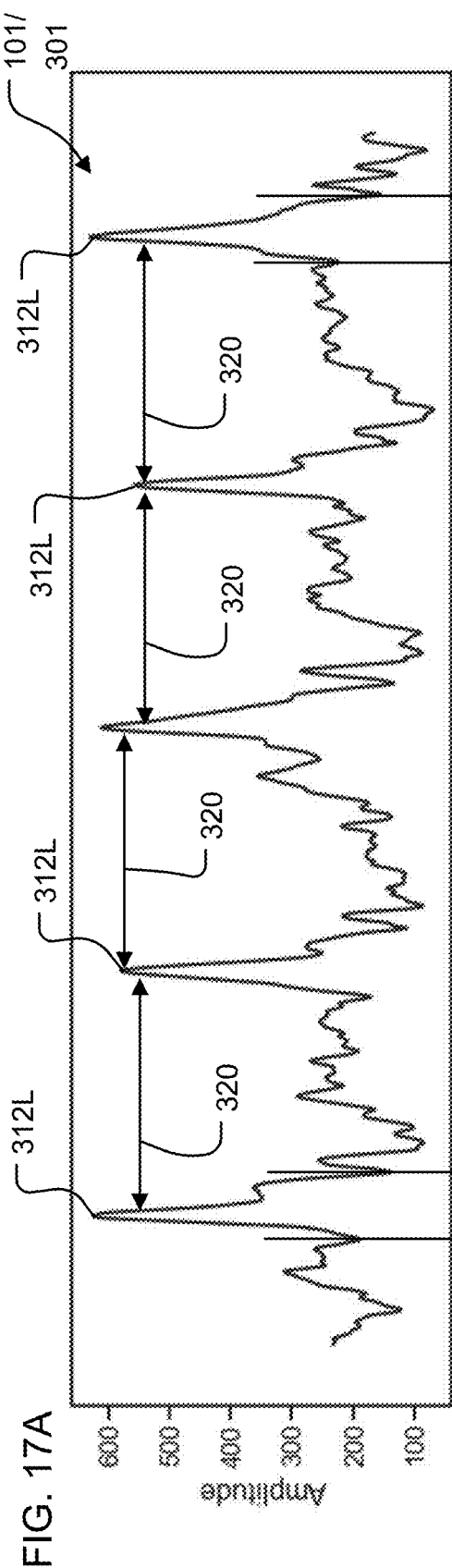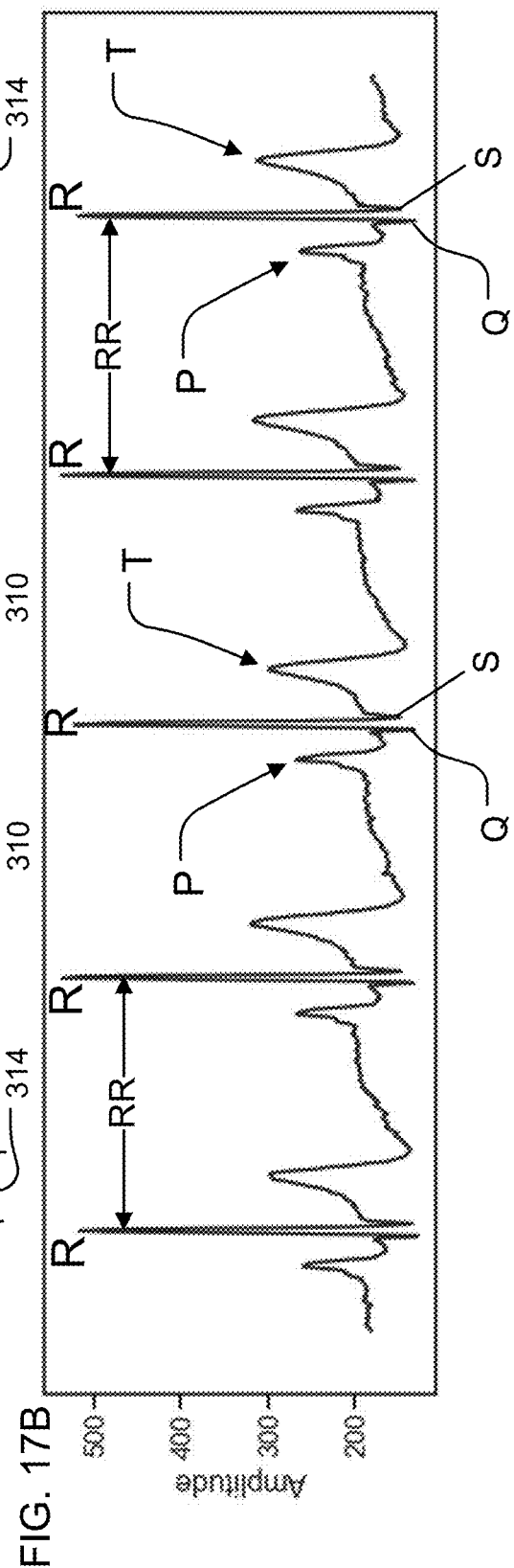
FIG. 17A
FIG. 17B

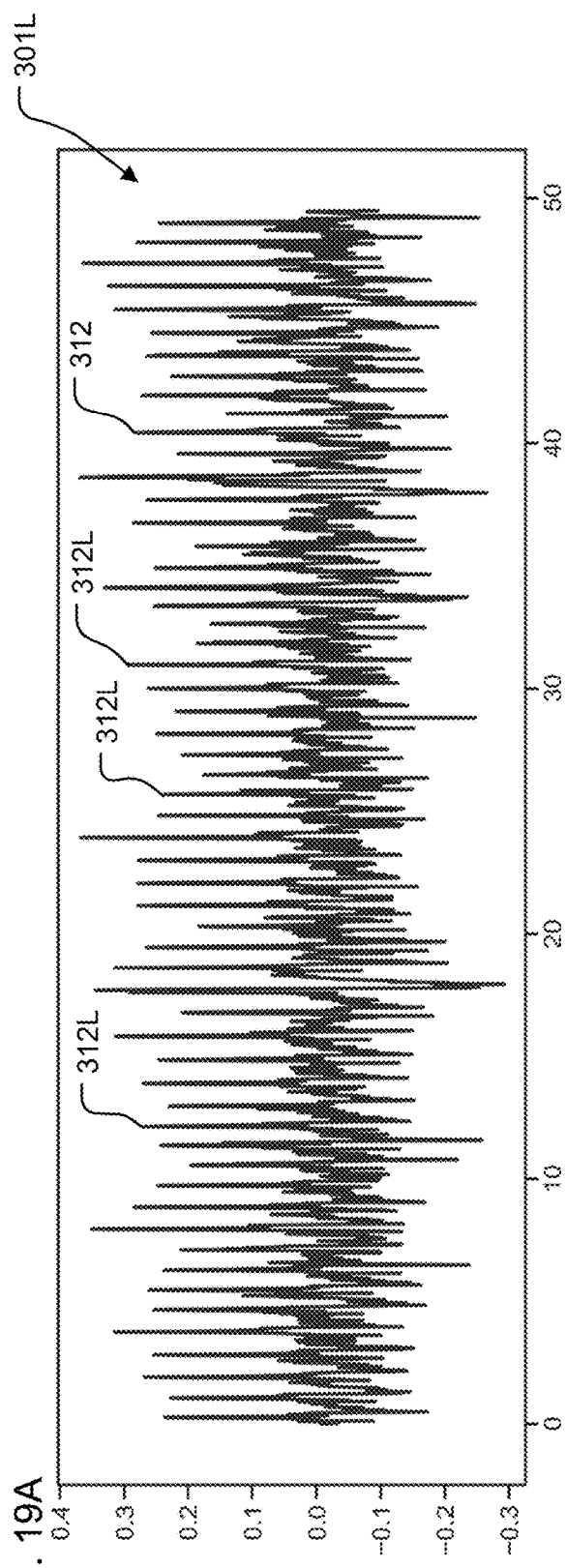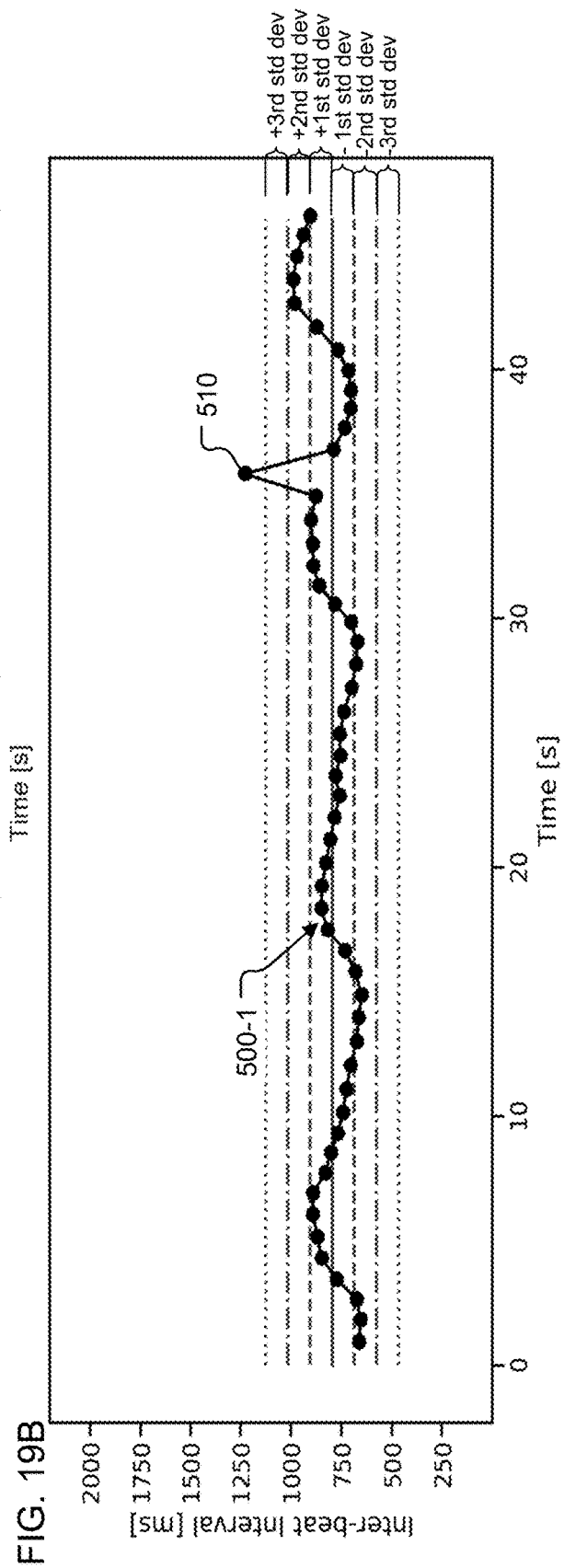

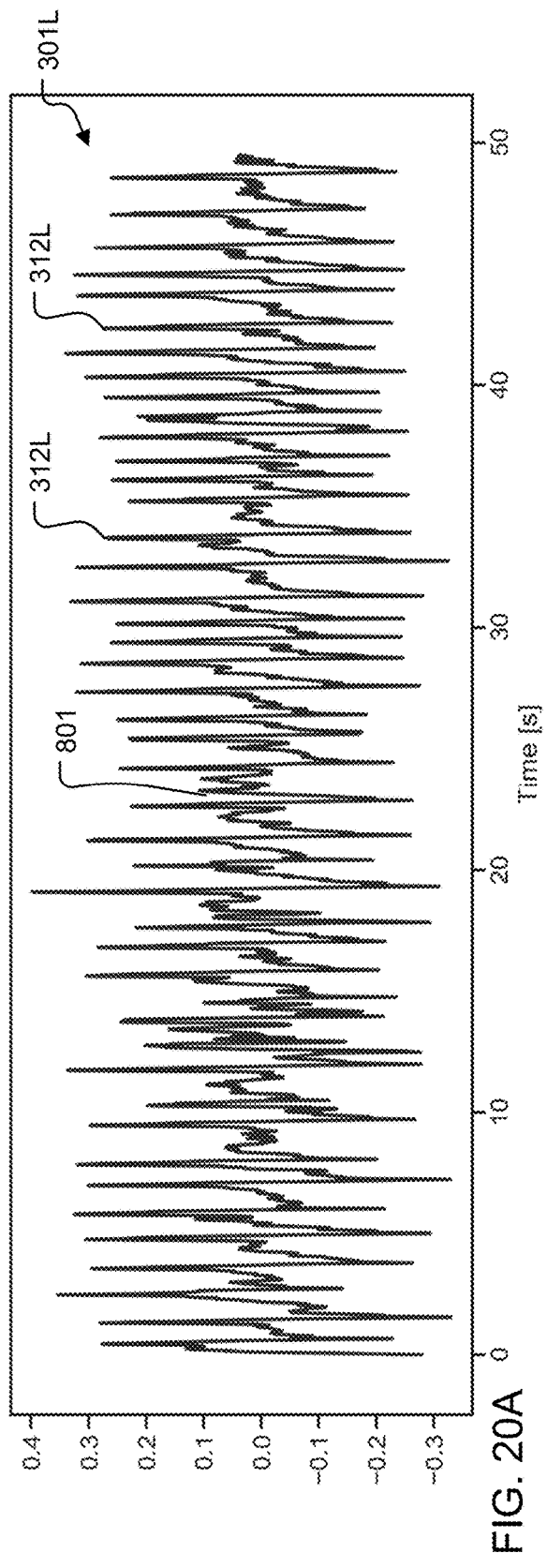
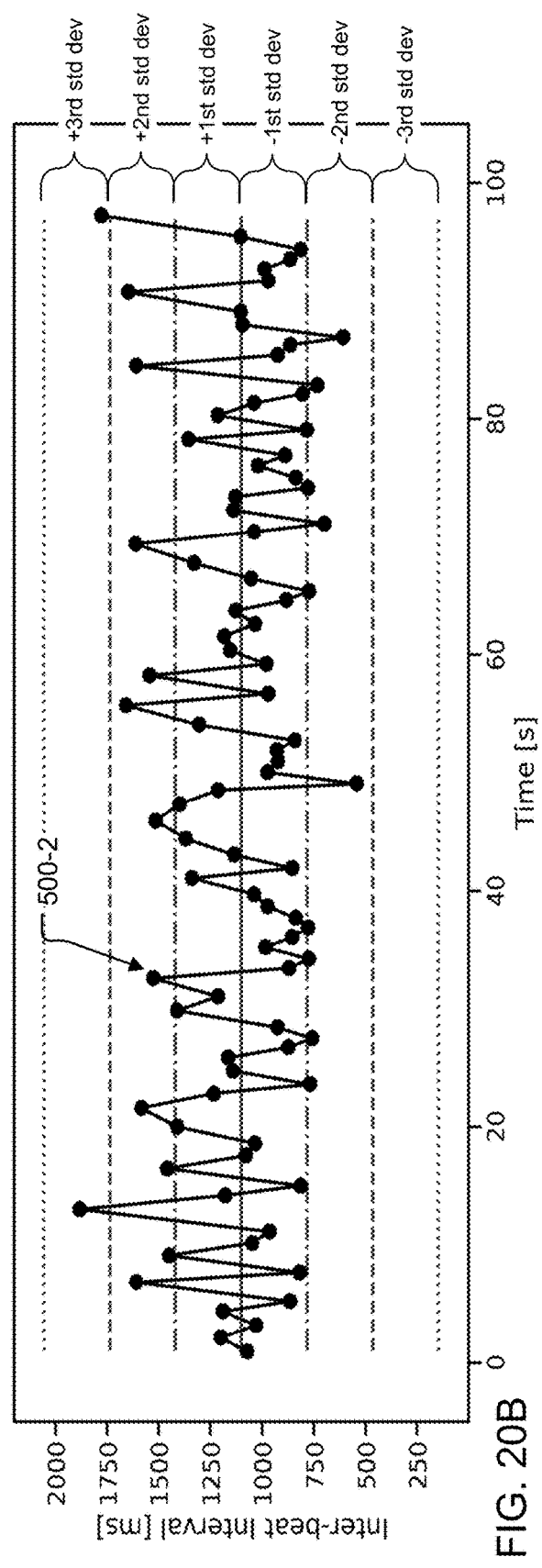
FIG. 20A
FIG. 20B

SYSTEM AND METHOD FOR HEART RHYTHM DETECTION AND REPORTING

RELATED APPLICATIONS

This application claims the benefit under 35 USC 119(e) of U.S. Provisional Application No. 62/876,341 filed on Jul. 19, 2019, which is incorporated herein by reference in its entirety.

This application is related to:

U.S. application Ser. No. 16/274,873, filed on Feb. 13, 2019, entitled "INFRASOUND BIOSENSOR SYSTEM AND METHOD," now U.S. Patent Publication No. 2019/0247010A1; and International Application number PCT/US2019/017832, entitled "INFRASOUND BIOSENSOR SYSTEM AND METHOD," now International Application Publication No. WO2019/160939A2.

All of the aforementioned applications are incorporated herein by reference in their entirety.

BACKGROUND OF THE INVENTION

The cardiovascular system of an individual is a network of blood vessels including arteries, veins, and capillaries that transport blood throughout the body. These blood vessels, together with the heart, form a closed-loop system for circulating the blood throughout the body, also known as the cardiovascular system. Function and status of the cardiovascular system is essential to human health.

The heart of a healthy adult individual beats at consistently the same rate or rhythm over time. In general, this heart rate is within the range of 60 to 100 resting heartbeats per minute (BPM). The time between successive heartbeats is also known as a heart cycle.

Normal sinus rhythm is a regular heart rhythm found in healthy people. A healthy respiratory sinus arrhythmia occurs when a person's heart rate relates to their breathing cycle. In other words, when the person breathes in, their heart rate increases, and when they breathe out, the rate decreases.

An arrhythmia is a medical condition associated with the heart rhythm of an individual. As compared to the heart rhythm of an average healthy individual of relatively the same age, an individual with a likely arrhythmia has a heart rhythm that is either too fast, too slow, irregular (i.e. skipping beats or erratic), or possibly a combination of these symptoms. At the same time, it is also possible that the normal heart rhythm of an individual is faster or slower than that of an average healthy individual, and yet the individual's heart is healthy (no arrhythmia is present).

Medical professionals use a variety of existing medical diagnostics systems to monitor and detect heart rhythms and to detect and clarify arrhythmias. These systems include electrocardiogram, Holter monitor, stress test, and implantable loop systems, in examples. The first three systems are non-invasive and use electrodes placed on the skin to detect electrical changes associated with heart operation. The implantable loop system, in contrast, requires subcutaneous implantation of an electrode-bearing device near the heart.

These medical diagnostics systems generally operate as follows. The electrodes detect small electrical changes that are a consequence of cardiac muscle depolarization followed by repolarization during each cardiac cycle. The electrical changes across multiple successive cardiac cycles are recorded or plotted, and a medical professional analyzes the plotted/recorded results to detect the heart rhythms and to determine whether an arrhythmia has occurred.

Of these systems, the electrocardiogram system is the standard medical diagnostics system for monitoring heart rhythm and determining whether arrhythmias exist. This system is setup and generally operates as follows. A medical professional typically attaches as many as 12 separate electrodes to various locations on the skin of the individual. The locations are near the torso, the heart and the upper arms. The individual is at rest during the procedure. For a time period of one minute or possibly even for just a few seconds, the system collects and records electrical signals sent from the electrodes, and plots a voltage of the electrical signal over time. The resulting voltage versus time plot is known as an electrocardiogram (ECG or EKG).

The Holter monitor system uses electrodes and operates in a substantially similar fashion as the electrocardiogram system, but the individual is monitored continuously for a period of hours (typically 12-48 hours). The individual can remain in the clinical setting during the monitoring, or can wear the electrodes at home over the monitoring period. The Holter monitor system is used when potential heartbeat issues require a longer time period to detect.

The stress test system is used to detect changes in the individual's heartbeat when the individual is active (under stress). In this system, the medical professional attaches electrodes to the torso and possibly even the arms and legs of the individual, and the individual walks at an increasing rate on a treadmill during the monitoring. An ECG of the individual's heart is obtained over the duration of the test.

The implantable loop system enables continuous monitoring and wireless reporting of an individual's heart rhythms over a period of months or years. This system is used to detect heartbeat problems that occur infrequently and would not be detected by the other systems. Individuals that have experienced strokes and infrequent but persistent fainting spells are generally candidates for this system. When the individual is sleeping, the implanted loop typically transmits the data collected over the same day via the Internet to your doctor or other medical professional.

Generally, there are three different classes of arrhythmias and different types within each class. The classes are bradycardia arrhythmias ("bradycardias"), tachycardia arrhythmias ("tachycardias"), and "extra heartbeats." The types of/within each of the classes are typically characterized by the areas or portions of the heart from which the heartbeat problems originate.

The bradycardias indicate a resting heart rate that is lower than 60 BPM and generally have two types. Though the heart rate is consistent/regular in pattern, it is typically too slow for the individual to breathe and function normally. The first type, sinus bradycardia, is the most common type of bradycardia and is caused by a disorder of the sinus node of the heart. Sinus bradycardias are rarely life-threatening and are usually treated by installing a pacemaker to increase the heart rate. The second type, heart block, is more dangerous. Heart block occurs when some or all of the electrical impulses generated by the sinus node are blocked before they reach the ventricles of the heart. Typically, heart block is most often accompanied by left bundle branch block or right bundle branch block.

The tachycardias indicate a resting heart rate that is typically higher than 100 BPM and have four types. Like the bradycardias, the tachycardias have a regular/consistent heart rate. However, the heart rate is typically too fast for the individual to breathe and function normally. The types of tachycardias include supraventricular tachycardias (SVT), ventricular tachycardias (VT, or V-tach) ventricular fibrillations (VF) and long QT syndrome.

The SVTs are typically the least severe type of tachycardias. The SVTs are caused by abnormal electrical activity occurring within or otherwise involving the atria portion of the heart. There are multiple subtypes of SVT, the most common being atrial flutter, atrial fibrillation (Afib), and Wolff-Parkinson-White syndrome. Though the SVTs are typically the least severe type of tachycardias, they can still be dangerous if untreated. If the SVTs persist over a matter of days, they can lead to heart damage and stroke, in examples.

Afib is also the most common of all arrhythmias in general. Its risk and severity increases with age. Of the SVT subtypes, Afib is the most chaotic and usually more difficult to treat. In addition, many individuals that have Afib experience few or vague symptoms. Individuals that experience shortness of breath or fatigue often believe they are "out of shape" or simply slowing down with age, when the root cause may be an underlying heart condition such as Afib. It is estimated that 50% of patients with Afib are unaware that they have it. Because of these reasons, Afib is a major focus of existing medical diagnostics systems.

The VT and VF tachycardias are the most life-threatening of the cardiac arrhythmias and often cause sudden cardiac death. While both the VTs and VFs are associated with rapid beating of the ventricles, the ventricular beats of VFs are random/uncoordinated and quickly lead to heart failure and death if not promptly treated. Patients that are at high risk for these arrhythmias are usually treated via an implanted defibrillator.

The long QT syndrome tachycardias are rare, genetically inherited tachycardias. The long QT syndrome tachycardias are associated with an unusually long QT interval of a heart signal obtained by an ECG.

The extra heartbeat arrhythmias can originate in different portions of the heart and generally have two types, atrial premature contractions and ventricular premature contractions. These arrhythmias are more commonly known as premature atrial complexes (PACs) and premature ventricular contractions (PVCs), respectively. The PACs originate in the atria, while the PVCs originate in one or more ventricles. The PVCs are the "skipped heartbeats" that can occur intermittently in virtually all individuals, especially when the individuals are under stress or have consumed stimulants such as caffeine or nicotine. While these arrhythmias are typically benign in nature, they can produce significant palpitations that some individuals find disruptive.

More recently, a consumer device worn around the wrist of individuals known as Apple Watch claims the ability to monitor heart rhythms and possibly detect arrhythmias. Apple Watch is a registered trademark of Apple Corporation. This device is attached to a wristband worn by the individual.

The Apple Watch has two versions that each operate generally as follows. In one version of the Apple Watch, the wristband includes optical sensors in the form of photodiodes. The photodiodes detect blood volume pulses in the wrist using photoplethysmography (PPG) and saves the information as "health data" that may indicate a possible arrhythmia. In a more recent version of the Apple Watch, a back portion of the device itself includes a single electrode that comes in contact with the individual's skin when worn. A crown of the watch includes a second electrode so that a single lead ECG can be obtained by placing a finger on the crown. These electrodes detect electrical signals associated with the heartbeat of the individual and the health data can be stored in response. Applications executing on the consumer device can then present the health data for display to a display screen of the device.

A computing device includes at least one or more central processing units (CPUs) and a memory. The CPUs have internal logic circuits that perform arithmetic operations and execute machine code instructions of applications ("application code") loaded into the memory. The instructions control and communicate with input and output devices (I/O) such as displays, printers and network interfaces.

The CPUs of the computing devices are typically configured as either microprocessors or microcontrollers. A microprocessor generally includes only the CPU in a physical fabricated package, or "chip." Computer designers must connect the CPUs to external memory and I/O to make the microprocessors operational. Microcontrollers, in contrast, integrate the memory and the I/O within the same chip that houses the CPU.

Computing devices that use microprocessors and microcontrollers are typically suited for different applications. Designers of microprocessor-based computing devices can choose from many different types and sizes of the external memory and I/O during system design. The microprocessors also typically have significant computing power, enabled by having multiple "cores" (i.e. multiple CPUs) within the microprocessors. The flexibility of configuration and computing power of microprocessors allows microprocessor-based computing devices to have many different configurations for use in a wide array of applications. In contrast, the integrated nature of the microcontrollers makes them especially suited for special-purpose computing devices such as embedded systems. In embedded systems, factors such as cost, physical size, and power and cooling are typically more important than computing power and flexibility.

The CPUs of the microcontrollers and microprocessors execute application code that extends the capabilities of the computing devices. In the microcontrollers, the application code is typically pre-loaded into the memory before startup and cannot be changed or replaced during run-time. In contrast, the CPUs of the microprocessors are typically configured to work with an operating system that enables different applications to execute at different times during run-time.

The operating system has different functions. The operating system enables application code of different applications to be loaded and executed at run-time. Specifically, the operating system can load the application code of different applications within the memory for execution by the CPU, and schedule the execution of the application code by the CPU. In addition, the operating system provides a set of programming interfaces of the CPU to the applications, known as application programming interfaces (APIs). The APIs allow the applications to access features of the CPU while also protecting the CPU. For this reason, the operating system 172 is said to execute "on top of" the CPU.

Other examples of CPUs include Digital Signal Processors (DSPs), Application Specific Integrated Circuits (ASICs), and Field Programmable Gate Arrays (FPGAs). The DSPs are pre-programmed, special-purpose microprocessors optimized for the requirements of digital signal processing.

The DSPs convert various types of input into digital signals, and perform operations upon the digital signals such as filtering, compression, conversion and transformation. The DSPs usually support analog to digital (A/D) and digital to analog (D/A) conversion and transformations including Fourier, Z, and wavelet transforms, in examples.

SUMMARY OF THE INVENTION

The medical diagnostics systems for monitoring heart rhythms and detecting arrhythmias present various levels of inconvenience and discomfort. In one example, these systems require that the individual at least attend a clinical setting/doctor's office in person. Though the systems other than the implantable loop system are non-invasive, they require the attachment and placement of multiple electrodes (possibly 12 or more) on various locations on the individual's skin. This is time-intensive and requires a trained technician or medical professional to properly set up, which increases complexity and cost. In another example, the systems other than the implantable loop are "one shot" systems: they monitor the heart rhythms of the individual for only a specific period of time.

Moreover, while the implantable loop system can monitor and report the heart rhythms of the individual continuously for a period of months or years, it is invasive and requires a surgical procedure. This surgical procedure carries risks, including the possibility of infection, damage to the heart and/or blood vessels, and bleeding, bruising, and pain at the implantation site.

The Apple Watch device also has limitations. In one example, the photodiodes of the PPG version of the Apple Watch are sensitive to movement, which affects the quality of the health data obtained. The optical sensors are also not as accurate as electrodes. Additionally, the wrist-pulse based heartbeats detected by the PPG version do not consistently track temporally with actual heartbeats, which leads to inaccurate results. In yet another example, the ECG version of the Apple Watch uses only a single lead (two electrodes), which results in poor signal quality and does not provide continuous monitoring like the PPG version. Rather, the ECG version requires that the individual open an app, place their finger on the watch, and collect health data for typically only 30 seconds.

Biosignals are signals in living beings such as individuals that can be detected, observed and/or measured. Examples of biosignals from individuals include acoustic signals, pressure signals, thermal signals and electrical signals, to name a few. The acoustic signals are created as a result of breathing and physical/mechanical operations within the individual's body. These operations include blood flow throughout the cardiovascular system, and opening and closing of valves within the heart and the blood vessels, in examples. These acoustic signals can be in either the infrasonic range (infrasonic signals) or in the audible range (audible signals) or both. The pressure signals are created by pressure or tension within the body. The thermal signals are created in response to physical and biochemical processes within the body. The electrical signals are associated with changes in electrical current over time, across a specialized tissue, organ, or cell system such as the nervous system. The ECG medical diagnostics systems detect these electrical signals.

A cardiology system for monitoring and analysis of heart rhythms ("cardiology system") is proposed. The cardiology system includes a biosensor system worn by an individual. In a preferred embodiment, the biosensor system is an in-ear biosensor system including at least one earbud placed at or within an ear canal of the individual. Typically, the in-ear biosensor system includes left and right earbuds. The in-ear biosensor system detects biosignals such as infrasound and pressure signals from the individual's body via various sensors of the earbuds.

The cardiology system also includes a data analysis system that receives the biosignals from the biosensor system. The data analysis system characterizes at least some of the signals as being associated with cardiovascular activity of the individual, such as pulse wave signals.

The pulse wave is a physiological phenomenon, observable and measurable in the arterial system during blood circulation. The pulse wave is a wave of increased pressure started by the ventricular systole radiating from semilunar valves over the arterial system. Typically, the pressure wave occurs at a rate varying between 20 and 30 feet (6.1 and 9.1 meters) per second in different arteries.

The pulse wave propagates through the arteries due to the reciprocal transformation between kinetic energy of a segment of blood volume expelled from the heart and the potential energy of a stretched segment of the resilient vascular wall of the arteries. The changes in pressure, blood flow, velocity and profile throughout the whole pulse wave can be detected and used for various purposes, including classification of artery elasticity, in one example.

Pulse wave signals are signals associated with the pulse waves that sensors of the biosensor system can detect. These signals are generally non-sinusoidal waveforms that include square waves and similarly periodic but asymmetrical waves. These pulse wave signals can be acoustic in nature or pressure based, in examples.

The data analysis system then analyzes the biosignals to detect heart rhythms and can determine whether arrhythmias exist based upon the heart rhythms.

The data analysis system can also classify the arrhythmias, update medical records in response to the analysis, and provide reporting/notification in the form of dispatching emergency personnel, contact medical professionals, and user feedback in visual and audible form, in examples.

The proposed cardiology system provides advantages over the existing medical diagnostics systems. As compared to the existing medical diagnostics systems, the proposed system is easier to use and setup, does not require an office visit, and is more comfortable. In addition, the proposed system is non-invasive, can be configured to monitor the individual over any time frame, and is significantly less expensive. At the same time, the proposed system detects heart rhythms and possible arrhythmias with an accuracy similar to that of ECG medical diagnostics systems, and may even exceed the accuracy of the ECG medical diagnostics systems.

As compared to the stress test, in one specific example, the proposed system has significant advantages. Often, the stress test is performed to trigger conditions or symptoms that patients might have experienced before coming to the doctor. Because the in-ear biosensor system of the proposed system is a wearable device, the patient can use it at home while experiencing symptoms. The system not only detects and analyzes heart rhythms and updates medical records in response, but can also be configured to automatically report data to a doctor and schedule a virtual appointment. Thus, the proposed system reduces the need for hospital and in-person clinical visits, allows for telehealth, and reduces the need for stress tests and patches.

The proposed cardiology system also provides advantages over the Apple Watch device and all other PPG-based heart rhythm detection systems. In examples, the proposed system is much more accurate and has greater data quality, and can be configured to monitor the individual over any time frame.

When the biosensor system is an in-ear biosensor system, the proposed heart rhythm system can provide feedback to the individual via the earbuds and/or a user device carried by the individual. The feedback can include issues during operation of and setup of the system, and results of the analysis, in examples.

Yet another advantage that the proposed cardiology system has over the Apple Watch device and all other PPG-based systems is that the proposed cardiology system is more likely to detect arrhythmias. When the biosensor system of the cardiology system is the in-ear biosensor system, in one example, the cardiology system can monitor the heart rhythms of individuals over any time frame, such as in a continuous fashion for minutes or perhaps hours, while they are using the system and its earbuds for other purposes (e.g. at rest listening to music or a phone call). As a result, the proposed system can continuously monitor the individual without the individual being aware that the monitoring is even taking place. For example, experimentation has shown that during testing, some individuals learned for the first time that they had arrhythmias. In contrast, the Apple watch requires the user to place their finger on the watch and in the clinical setting the physician must order an ECG or Holter monitor. Therefore, the proposed system is more likely to find arrhythmias that have been previously undiagnosed. This is especially important in the case of Afib.

In another embodiment, the biosensor system of the proposed cardiology system is in the form of a patch worn on or against the skin of the individual. The patch includes similar sensors as in the in-ear biosensor system or possibly different sensors. The patch is typically placed on the skin near major arteries such as the brachial, radial, femoral, and carotid arteries, in examples. The patch can be affixed directly to the skin via a temporary adhesive, or held in place against the skin via a cuff or elastic placed around a finger, arm, head or leg. In one particular example, the patch biosensor system forms a wrist-worn device for monitoring heart rhythms of the individual by detecting biosignals via a radial artery of the individual.

In general, according to one aspect, the invention features a cardiology system for detecting and analyzing heart rhythms. The system includes a biosensor system worn by an individual and a data analysis system. The biosensor system includes sensors that detect biosignals including infrasonic signals from the individual. The data analysis system receives the biosignals from the biosensor system and determines heart rhythms of the individual based upon the biosignals.

In a preferred embodiment, the biosensor system is an in-ear biosensor system that includes at least one earbud. The at least one earbud includes the sensors that detect the biosignals including the infrasonic signals. The in-ear biosensor system can also include an auxiliary sensor for detecting pressure biosignals in the ear of the individual to monitor occlusion level of the at least one earbud, and to monitor physiological changes of the individual. The in-ear biosensor system can also detect the biosignals from left and right earbuds for improving a signal to noise ratio of the biosignals. In another embodiment, the biosensor system is a patch worn on or against the skin of the individual.

In one example, the data analysis system can determine heart rhythms of the individual based upon the biosignals by detecting pulse wave signals in the biosignals, determining inter beat intervals of the heart based upon the pulse wave signals, and computing the heart rhythms from the inter beat intervals. In another example, the data analysis system can determine heart rhythms of the individual by detecting pulse wave signals in the biosignals, calculating stroke volumes under each of the pulse wave signals during systole times, and computing the heart rhythms from changes in the stroke volumes.

The data analysis system can determine arrhythmias including atrial fibrillation (Afib) arrhythmias by detecting pulse wave signals in the biosignals and characterizing the overall pulse wave signal shape and changes in the pulse wave signal shape over time. The data analysis system can also determine arrhythmias including atrial fibrillation (Afib) arrhythmias from the heart rhythms.

The cardiology system can also detect other cardiovascular events and characteristics and provide measurements associated with the events and characteristics. The events and characteristics include mitral valve closing, aortic valve opening and closing, and vasculature of aorta and arteries, in examples. The system can also measure turbulent flows and shape of the waveforms of the biosignals, in examples. These cardiovascular events and characteristics and measurements can also be used along with stroke volume and inter beat intervals to characterize different types of arrhythmias.

The data analysis system can identify and remove motion artifacts associated with motion of the individual from the biosignals prior to determining the heart rhythms of the individual. Also, the data analysis system can distinguish premature ventricular contractions (PVCs) from premature atrial complexes (PACs) and distinguishes supraventricular tachycardias (SVT) from ventricular tachycardias (VT).

Typically, the cardiology system includes at least one user device. The user device may be carried by the user. The user device includes a cardiovascular user application (user app) executing upon a CPU of the user device, and the user app communicates with the biosensor system to control the sending of the biosignals to the data analysis system.

The data analysis system and the functions it provides can be included within or distributed across multiple devices or components of the cardiology system. In one implementation, the data analysis system is distributed across one or more computer nodes in a remote network. In another implementation, the data analysis system is included within one or more user devices. In yet another implementation, the data analysis system is included within the biosensor system. In still another implementation, the data analysis system is distributed across a user device and at least one computer node of a remote network.

In general, according to another aspect, the invention features a method for detecting and analyzing heart rhythms. Here, the method detects biosignals including infrasonic signals from the individual, via sensors of a biosensor system worn by the individual. The method then determines heart rhythms of the individual based upon the biosignals.

In examples, the method also can update a medical record of the individual in response to determining the heart rhythms of the individual, and notify health care and safety professionals in response to determining the heart rhythms of the individual.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 2B is a block diagram that shows detail for a medical record in FIG. 1;

FIG. 2C is a block diagram that shows detail for a user account in FIG. 1;

FIG. 15A through 15C are single-channel plots of pulse wave signals for the same individual, determined in accordance with the method of FIG. 12, where FIGS. 15A and 15B are plots of pulse wave signals that were obtained by the left and right earbuds, and FIG. 15C combines the plots of FIGS. 15A and 15B;

FIGS. 15D and 15E are single-channel plots of pulse wave signals for a healthy individual and an individual diagnosed with atrial fibrillation, respectively;

FIG. 15F shows pulse wave signals for an individual with regular heart rhythms obtained by left and right earbuds, where the signals are characterized by similar lengths of inter beat intervals in the left and right pulse wave signals;

FIG. 17A is a single-channel plot of pulse wave signals of an individual detected in accordance with the method of FIG. 12, and FIG. 17B is an ECG plot of heart operation of the same individual obtained by standard ECG medical diagnosis equipment, where the individual was the subject of both testing methods at substantially the same time and over the same duration;

FIG. 19A is a single-channel plot of pulse wave signals of a healthy individual detected in accordance with the method of FIG. 12, where at least 57 successive pulse wave signals over a period of approximately 50 seconds are shown;

FIG. 19B is a standard inter beat intervals/heart rhythm plot created from the pulse wave signals of the healthy individual in FIG. 19A, where the individual's inter beat intervals are presented in milliseconds (ms) over time, and where a waveform of the inter beat intervals shows a non-arrhythmia condition;

FIG. 20A is a single-channel plot of pulse wave signals of an unhealthy individual detected in accordance with the method of FIG. 12, where at least 45 successive pulse waves over a period of approximately 50 seconds are shown;

FIG. 20B is a standard inter beat intervals/heart rhythm plot created from the pulse wave signals of the unhealthy individual in FIG. 20A;

FIG. 22A uses an inter beat interval median absolute deviation statistic; FIG. 22B uses a pNN50 heart rate variability statistic; FIG. 22C uses an RMSSD/Mean statistic; and FIG. 22D uses a pNN20 heart rate variability statistic.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
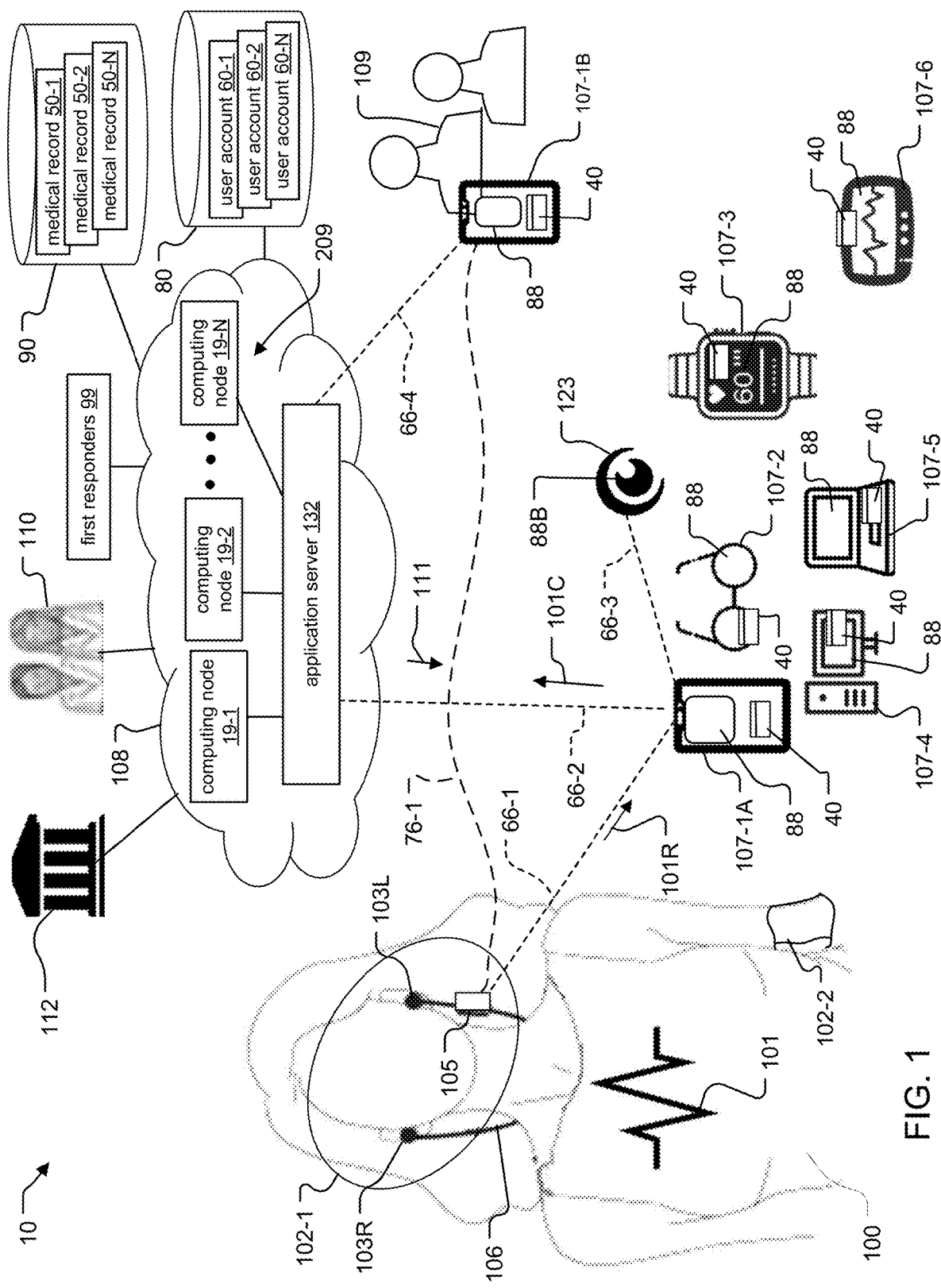
FIG. 1 is a schematic diagram of an exemplary cardiology monitoring and analysis system ("cardiology system") constructed according to principles of the present invention, where the diagram shows two different embodiments of biosensor systems of the cardiology system worn by an individual, the biosensor systems including an in-ear biosensor system and a patch biosensor system, and where the diagram also shows a cloud-based data analysis system of the cardiology system.

FIG. 1 shows an exemplary cardiology system 10 for detecting, monitoring and analyzing heart rhythms of individuals 100. The cardiology system 10 detects biosignals 101 from the individual's body, and characterizes at least some of the signals as being associated with cardiovascular activity of the individual 100.

The cardiology system 10 includes a biosensor system 102 worn by an individual. The biosensor system includes sensors that detect biosignals 101 including infrasonic signals from the individual 100 and a data analysis system 209. The data analysis system receives the biosignals from the biosensor system, and determines heart rhythms of the individual based upon the biosignals.

The cardiology system 10 analyzes the biosignals 101 to determine heart rhythms of the individuals. The system 10 can classify the heart rhythms, and notify the individual 100 and various other persons of potentially life-threatening arrhythmias detected during the analysis of the heart rhythms. In particular, the system 10 detects and reports Afib arrhythmias. The system 10 also stores information resulting from the analysis for future reference and analysis by the system 10.

The cardiology system 10 has various components. These components include the biosensor system 102, such as an in-ear biosensor system 102-1 worn by the individual 100, the data analysis system 209 and at least one user device 107. The components also include an application server 132, a medical record database 90 and a user database 80. Various facilities 112, first responders 99, health care and safety professionals 110, and user devices 107 carried by other individuals 109 are also shown. A network cloud 108 enables connections between these various components.

The in-ear biosensor system 102-1 includes at least one earbud. The earbud includes the sensors that detect the biosignals 101 including infrasonic signals. Preferably, as shown in the figure, the in-ear biosensor system 102-1 includes left and right earbuds 103L, 103R and a controller board 105. The earbuds 103 communicate with one another and with the controller board 105 via earbud connection 106. Here, the earbud connection 106 is a wired connection.

The biosensor system 102 can also be a patch biosensor system worn on or against skin of the individual 100. In the illustrated example, patch biosensor system 102-2 is part of a cuff or elastic fabric worn around the elbow of the individual 101. The sensors of the patch are placed against the skin, adjacent to the brachial artery.

In one implementation, as shown in the figure, the data analysis system 209 and the application server 132 are located within the network cloud 108. The data analysis system 209 includes one or more computing nodes 19-1 . . . 19-N that are distributed across one or more networks within the network cloud 108. Alternatively, the computing nodes 19 and/or the server 132 might also be located on a local area network within a premises, such as a residence, commercial building or place of business of the individual 100.

The application server 132 is a computing device that communicates with various components. These components include the user devices 107 and the data analysis system 209. In addition, because the server 132 is within the network cloud 108, the server 132 can communicate with the facilities 112, the health care and safety professionals 110, the first responders, and the databases 80/90.

The user devices 107 include portable user devices and stationary user devices. In examples, the portable user devices include a mobile phone 107-1A, smart glasses 107-2, a smart watch 107-3, and a laptop 107-5. The stationary user devices include a workstation 107-4 and a gaming system 107-6, in examples.

Each user device 107 is a computing device that includes a display 88 and one or more applications. An interactive application running on each user device 107, a cardiovascular user application (user app) 40, is shown. The user app 40 of each user device 107 receives information sent by other components in the system 10 and presents a graphical user interface (GUI) on the display 88. The GUI allows the individual 100 to enter information for the user app 400 and can display various information upon the display 88. The user app 40 might also control other components in the system 10.

Also shown are a bionic contact lens 123 having a display 88B and other individuals 109 carrying user devices 107 (here, smart phone 107-1B).

The facilities 112, the first responders 99, the health care and safety professionals 110, the user database 80, and the medical record database 90 connect to the network cloud 108. These connections could be wired Internet-based or telephony connections, wireless cellular connections, and/or wireless Internet-based connections (e.g. Wi-Fi), in examples.

The medical record database 90 includes medical records 50 of the individuals 100 and the user account database 80 includes user accounts 60 of the individuals 100. The facilities include medical facilities such as hospitals, clinics and private medical offices. The health care and safety professionals 110 include medical professionals such as doctors and nurses. The first responders 99 include police, fire, and possibly other emergency response personnel.

The biosensor systems 102-1 and the user devices 107 communicate with each other and with the network cloud 108 via wireless communications links 66. In one example, the user device 107-1A connects to the in-ear biosensor system 102-1 via wireless link 66-1, and connects to the application server 132 via wireless link 66-2. The user device 107-1A might also present information for display upon display 88B of bionic contact lens 123 via wireless link 66-3. In a similar fashion, the user device 107-1B connects to the application server 132 via wireless link 66-4. The wireless links 66 might be cellular-based (e.g. 5G cellular networks or prior generations of wireless network) or Internet-based (e.g. IEEE 802.11/Wi-Fi, or possibly even Bluetooth).

Additionally, the in-ear biosensor system 102-1 might establish peer-to-peer (P2P) wireless links 76 to one or more other user devices 107. In this way, the user devices 107 can form either predetermined or ad hoc networks of the user devices 107. P2P wireless link 76-1 between user device 107-1A and 107-1B is shown. The wireless links 76 might use various wireless communications including Bluetooth/Bluetooth Low Energy (BLE), ZigBee, and Wi-Fi NFC, in examples.

Infrasounds

Biological acoustic signals are generated internally in the body by for example breathing, heartbeat, coughing, muscle movement, swallowing, chewing, body motion, sneezing, blood flow, etc. Audible and infrasonic sounds can be also generated by external sources, such as air conditioning systems, vehicle interiors, various industrial processes, etc.

Acoustic signals represent fluctuating pressure changes superimposed on the normal ambient pressure, and can be defined by their spectral frequency components. Sounds with frequencies ranging from 20 Hz to 20 kHz represent those typically heard by humans and are designated as falling within the audible range. Sounds with frequencies below the audible range (i.e. from 0 Hz to 20 Hz) are termed infrasonic. The level of a sound is normally defined in terms of the magnitude of the pressure changes it represents. These changes can be measured and do not depend on the frequency of the sound. The biologically-originating sound detected inside the ear canal by the earbuds 103 is mostly in the infrasound range.

The left and right earbuds 103L,103R detect biosignals 101 including infrasonic signals from the individual 100 via sensors included within one or more of the earbuds 103. These sensors include acoustic sensors including infrasound and vibration sensors, and pressure sensors, in examples. In particular, the infrasound and vibration sensors detect biosignals 101 associated with operation of the cardiovascular system of the individual 100 and send the biosignals 101 for analysis to the data analysis system 209.

The in-ear biosensor system 102-1 detects biosignals 101 from the left and right earbuds 103L,R. Typically, the biosignals 101 are detected at each of the earbuds 103L,R at substantially the same times. This "stereo effect" can be utilized to improve a signal to noise ratio of the biosignals 101 and thus more robustly identify biosignals associated with cardiovascular activity.

The data analysis system 209 receives the biosignals 101 from the earbuds 103 and characterizes at least some of these signals as being associated with cardiovascular activity of the individual 100. Experimentation has shown that many if not most of the biosignals 101 are infrasonic in nature and are associated with cardiovascular activity.

The application server 132 determines whether individuals 100 are authorized users of the system 10. For this purpose, the individuals 100 wear user devices 107 that include credentials that identify the individuals. These credentials can be in the form of a username and password, and/or biometric identifier such as a fingerprint or iris scan, in examples. Via the user apps 40 on the user devices 107, the user devices 107 send the credentials over the wireless link 66 to the application server 132. The server 132 then compares the credentials to stored credentials for the users in the user account database 80. The stored credentials for the users are located in separate user accounts 60-1 . . . 60-N within the user account database 80.

The system 10 in FIG. 1 generally operates as follows. With reference to the in-ear biosensor system 102-1, for example, the earbuds 103L,103R detect and collect the biosignals 101 from the individual 100 and send the signals 101 to the controller board 105. The controller board 105 buffers the biosignals 101 for subsequent transmission via a wireless interface of the controller board 105. The individual 100 then accesses the user app 40 of a user device 107, such as smart phone user device 107-1A worn/carried by the individual 100. The individual 100 enters his/her credentials in the user app 40, which in turn establishes an authenticated login session over wireless connections 66-2 between the user app 40 and the application server 132. An authenticated individual 100 is a valid user of the system 10.

Once the individual 100 is authenticated, the user app 40 establishes wireless connection 66-1 between the user device 107-1A and the controller board 105. The user app 40 then sends various commands over the wireless connection 66-1 to the controller board 105. Some of these commands control transmission of the biosignals 101 from the controller board 105 over the wireless connection 66-1 to the user device 107-1. Here, the biosignals 101 are typically in "raw" (uncompressed) format 101R. The user device 107-1A compresses the raw signals 101R and sends a compressed version of the signals 101C over the wireless connection 66-2 to the application server 132.

The application server 132 decompresses the compressed biosignals 101C and forwards the signals 101 to the computing nodes 19 that form the data analysis system 209. The data analysis system 209 characterizes at least some of the biosignals 101 as being associated with cardiovascular activity, analyzes the biosignals 101 to detect heart rhythms of the individual and can determine whether an arrhythmia has occurred from the heart rhythms. The data analysis system 209 can also classify the type of arrhythmia. The data analysis system 209 or the application server 132 can access and update the medical record 50 of the individual 100 during and in response to the analysis. As a result, the cardiology system 10 can update a medical record 50 of the individual 100 in response to determining the heart rhythms of the individual 100.

After determining the heart rhythms, the data analysis system 209 might determine that an arrhythmia has occurred or detect another likely heart problem. In response, the data analysis system 209 can notify the health care and safety professionals 110 and the first responders 99. For this purpose, the data analysis system 209 might send notification messages 111 that include information concerning the analysis and the results of the analysis to the health care and safety professionals 110, and initiate an emergency phone call via the 911 system to contact the first responders 99, in examples. The notification messages 111 can be in the form of an email, SMS/text message, phone call, or possibly even audible speech, in examples. Thus, the cardiology system 10 can notify the health care and safety professionals 110 in response to determining the heart rhythms of the individual 100.

The data analysis system 209 can also notify the individual 100 both during and after the analysis via the notification messages 111. Here, the user app 40 receives the notification messages 111 and might present the notification messages 111 at the display 88, or forward the messages 111 over the wireless link 66-1 to the in-ear biosensor system 102-1, in one example. In this way, the earbuds 103L, 103R could relay audible information to the individual 100 concerning operation of the system 10, in one example.

As a result, the cardiology system 10 can automatically monitor and detect heart rhythms of individuals 100 and identify possible arrhythmias from the heart rhythms, classify the arrhythmias, update medical records 50, report problems/notify first responders 99 and health care and safety professionals 110, and provide feedback to the individuals 100 during the detection and upon completing the analysis.

Figure 2A:
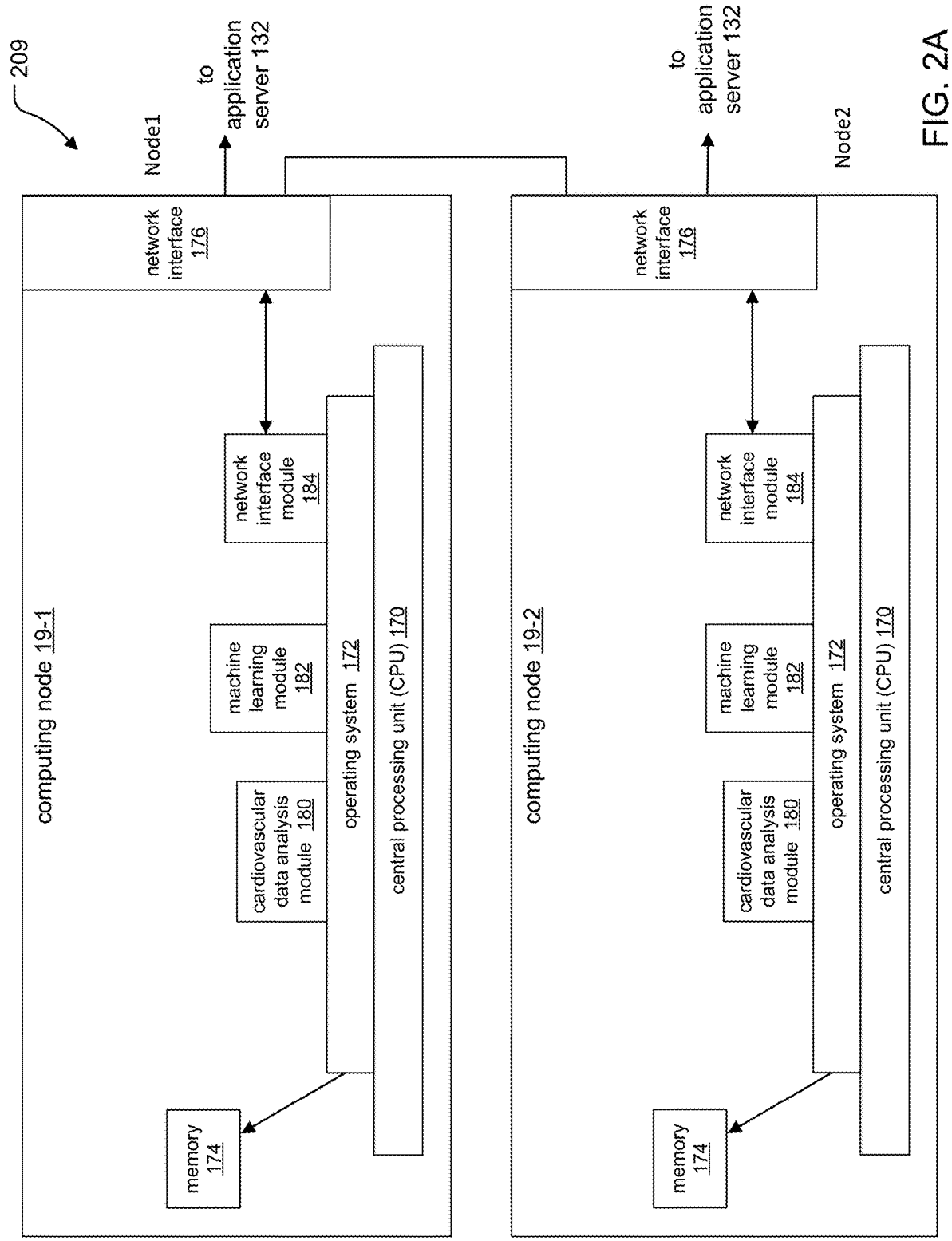
FIG. 2A is a block diagram that shows detail for the data analysis system in FIG. 1.

FIG. 2A shows details for the cloud-based data analysis system 209 in FIG. 1. Two computing nodes 19-1 and 19-2 are shown. The computing nodes 19-1, 19-2 are both computing devices. In one implementation, the computing nodes 19-1 and 19-2 share the computational processing required during analysis of the biosignals 101 of the individual 100.

The computing nodes 19-1, 19-2 are both configured as microprocessors and include substantially the same components. These components include a central processing unit (CPU) 170, an operating system 172, a memory 174, a network interface 176, and various software applications. The software applications include a cardiovascular data analysis module 180, a machine learning module 182, and a network interface module 184.

The network interface module 184 communicates with the network interface 176. The network interface 176, in turn, connects to the application server 132.

FIG. 2B shows detail for a medical record 50 of an individual 100 stored in the medical record database 90. The medical record 50 includes various fields. These fields include user data 902, biometric data 904, insurance data 906, a baseline heart rhythm 920, and a derived heart rhythm 922.

In more detail, the user data 902 includes information such as a name, address, and telephone/contact for the individual. The biometric data 904 might include a biometric identifier (ID) such as a fingerprint or iris scan for identifying the individual 100. The insurance data 906 includes the type of insurance that the individual 100 carries. The baseline heart rhythm 920 is typically a tachogram or other plot of heart rhythm that establishes a baseline level of heart operation for the individual 100. The derived heart rhythm 922 typically includes information sent from the data analysis system 209 after analysis of the individual's heart rhythms.

FIG. 2C shows detail for a user account 60 of an individual 100 stored in the user account database 80. The user account 60 includes various fields. These fields include credentials 907, a biosensor system version 962, and a version of the user app 964.

In more detail, the credentials 907 include information such as a username/password and/or biometric ID, or telephone/contact for the individual 100. The biosensor system version 962 can be used to compare/contrast capabilities of and to track various released versions of the biosensor system 102 over time. In a similar vein, the user app version 964 can be used to compare/contrast capabilities of the user app 40 currently installed on each user device 107 and to track various released versions.

Figure 3:
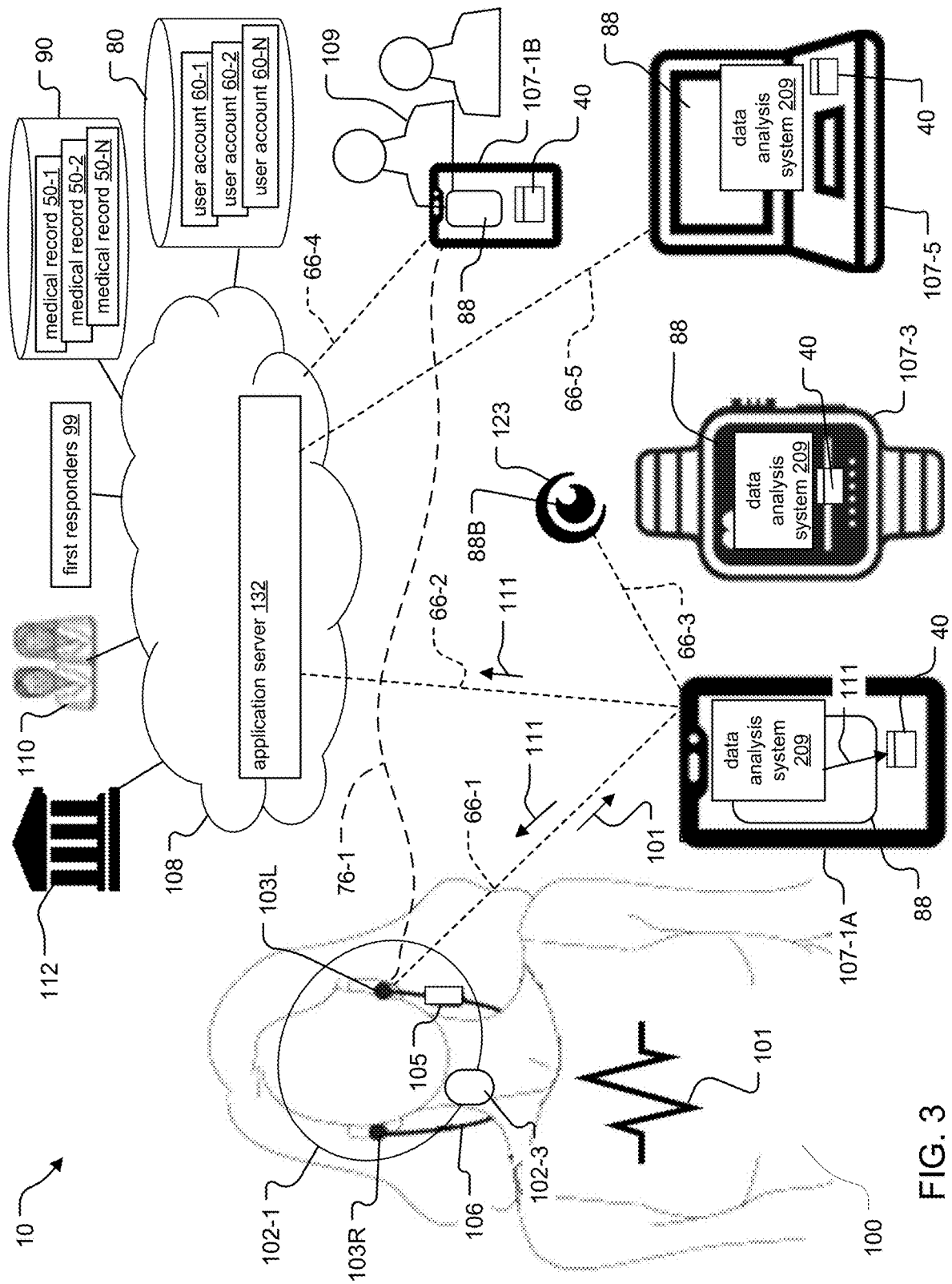
FIG. 3 is a schematic diagram of another exemplary cardiology system, where the data analysis system is located within a user device (e.g. smart phone) carried by the individual.

FIG. 3 shows another exemplary cardiology system 10. The system 10 includes similar components and operates in a substantially similar fashion as the system in FIG. 1. However, there are differences.

Here, the data analysis system 209 is located within/distributed across one or more user devices 107. Only user devices 107-1, 107-3, and 107-5 are shown. In the figure, a data analysis system 209 is included within smart phone 107-1A carried by the individual 100, and within user devices 107-2 and 107-5. User device 107-5, a laptop, communicates with the application server 132 via wireless link 66-5.

Patch biosensor system 102-3 is also shown. In the illustrated example, biosensor system 102-3 is removably attached to skin on the side of the individual's neck near one of the carotid arteries. The patch biosensor system 102-3 is attached using a coupling agent such as a gel that provides an airtight seal between the sensors of the biosensor system 102-3 and the skin. Because the gel also operates as a coupling agent, biosignals 101 can transmit through the gel for detection by the sensors of the biosensor system 102-3 with minimal signal loss.

In one example, one or more applications executing on the CPU of each user device 107 implements or otherwise provides the operations of the data analysis system 209. In another example, firmware and/or a combination of firmware and applications can be used.

The system 10 of FIG. 3 operates in a similar fashion as in FIG. 1, with some differences. As in FIG. 1, the user app 40 authenticates the individual 100, establishes wireless connection 66-1 between the user device 107-1A and the controller board 105, and instructs the in-ear biosensor system 102-1 or patch biosensor system 102-3 to send the detected biosignals 101 over the wireless connection 66-1 to the user device 107-1A for analysis. In FIG. 3, however, the data analysis system 209 is within user device 107-1A. The data analysis system 209 of the user device 107-1A sends the notification messages 111 to the user app 40, the in-ear biosensor system 102-1 or patch biosensor system 102-3, and the first responders 99/health care and safety professionals 110.

The cardiology system 10 of FIG. 3 can also distribute the characterization and/or analysis operations across data analysis systems 209 of different user devices 107. In one example, the system 10 might distribute some of these operations at the data analysis systems 209 of user device 107-A, and other operations at the data analysis systems 209 of user devices 107-3 and 107-5. For this purpose, the user devices might include resource utilization, reservation and management capabilities. For example, user device 107-A1 operating as a leader device could establish a wireless ad-hoc network with the other user devices 107 as follower devices, and query them to assess their capabilities including processing power, processor types (e.g. separate image processing or DSP device from the CPU), and available memory and/or storage capabilities, in examples. The leader device could then distribute the analysis of the biosignals 101 over the ad-hoc network to the data analysis systems 209 of one or more of user devices. The leader device can distribute the analysis over different user devices 107 based on specific capabilities reported by the leader and the follower devices, or a combination of the capabilities of the leader and follower devices best matching the analysis required.

Figure 4:
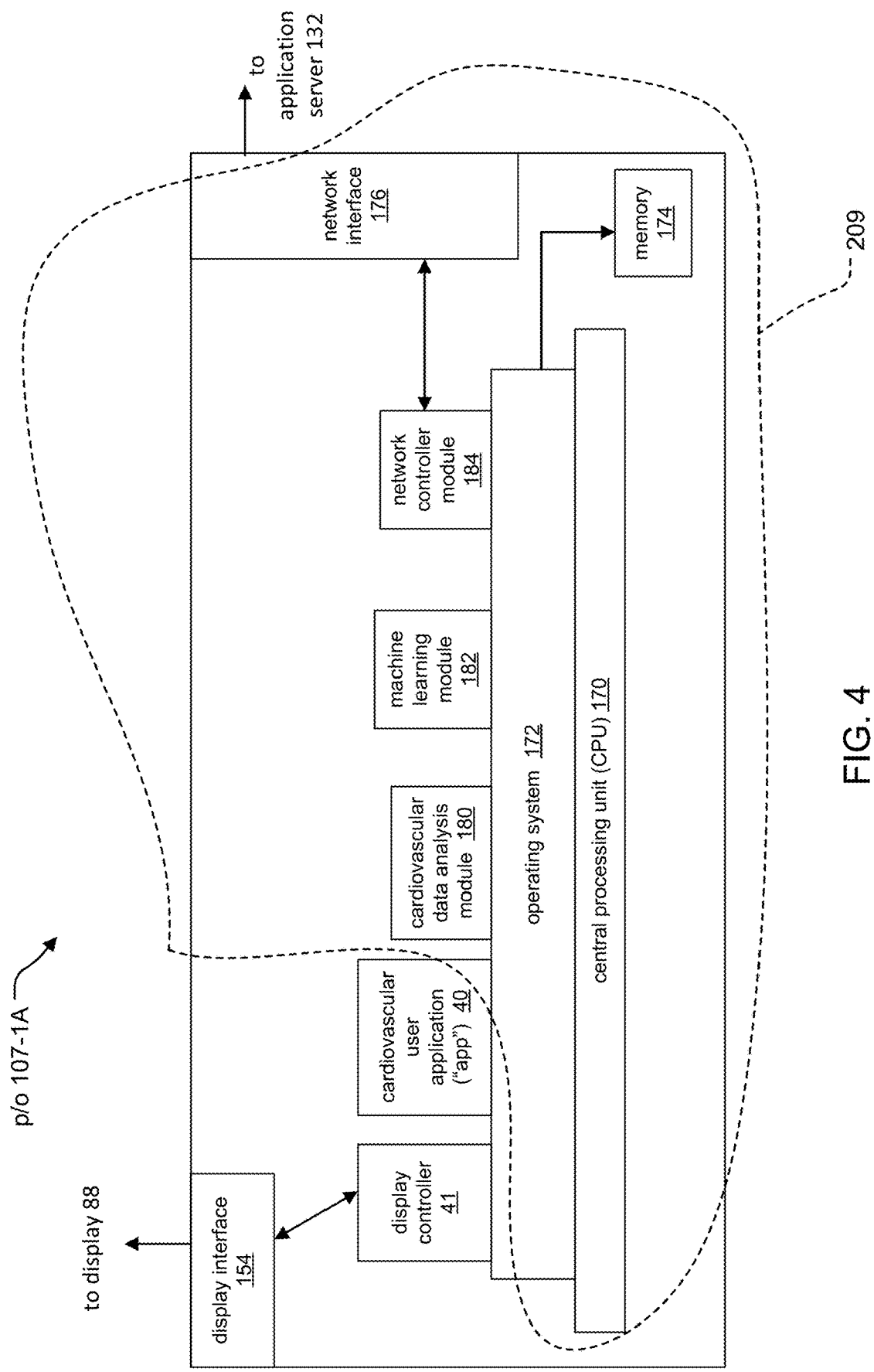
FIG. 4 is a block diagram showing detail for components of the data analysis system in FIG. 3.

FIG. 4 shows more detail for smart phone user device 107-1A in the cardiology system 10 of FIG. 3. The smart phone 107-1A is a computing device that is configured as a microprocessor and includes similar components as the computing nodes 19 in FIG. 2A. The similar components are the central processing unit (CPU) 170, operating system 172, memory 174, network interface 176, and various applications. Here, the applications are software applications, but the applications could also be included in firmware. The applications include the cardiovascular data analysis module 180, the machine learning module 182, and the network interface module 184.

The smart phone user device 107-1A also includes a display interface 154 and a display controller 41 software application. The display interface 154 communicates with the display controller 41. The display interface 154, in turn, connects to the display 88 of the user device 107-1A.

Also shown is the data analysis system 209 located within the user device 107-1A. Here, the data analysis system 209 is formed from at least the same components as those within the computing nodes 19 that form the data analysis system 209 of FIG. 2A.

Figure 5:
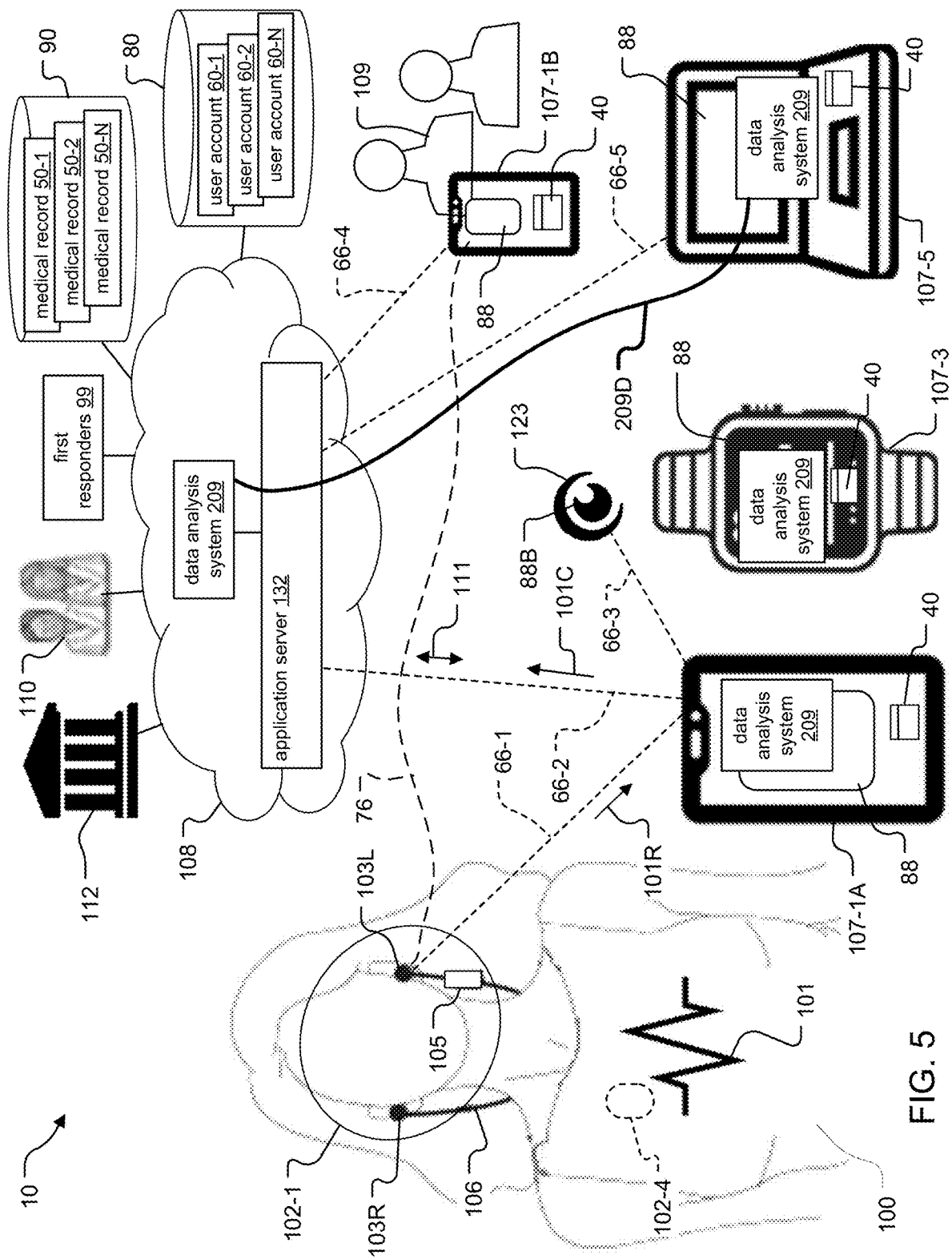
FIG. 5 is a schematic diagram of another exemplary cardiology system, where the data analysis system is distributed across the cloud-based network and at least one user device.

FIG. 5 shows yet another cardiology system 10. The system 10 combines aspects of the cardiology systems in FIG. 3 and FIG. 4 to provide a data analysis system 209D that is distributed across at least one user device 107-5 and the cloud network 108.

In more detail, the cloud-based network 108 and at least one user device 107-5 both include a data analysis system 209, which together form a distributed data analysis system 209D. Alternatively, both the cloud-based network 108 and at least one user device 107-5 include computing nodes 19 that form a distributed data analysis system 209D.

Patch biosensor system 102-4 is also shown. Here, biosensor system 102-3 is removably attached to skin near the individual's heart.

The system 10 generally operates as follows. Using the in-ear biosensor system 102-1 as an example, the user app 40 authenticates the individual 100, establishes wireless connection 66-1 between the user device 107-1A and the controller board 105, and instructs the in-ear biosensor system 102-1 to send the biosignals 101 over the wireless connection 66-1 to the user device 107-1A. At the user device 107-1A, the user app 40 might instruct the data analysis system 209 local to user device 107-1A to characterize at least some of the biosignals 101 as being associated with cardiovascular activity, analyze a portion of the biosignals 101, and send another portion of the signals 101 to the application server 132 for analysis by the distributed data analysis system 209D. Here, the data analysis system 209 local to user device 107-1A and/or the distributed data analysis system 209D could carry out the analysis and classification of the biosignals 101, update the medical records 50, and execute the various notification/reporting functions, in one example.

Figure 6:
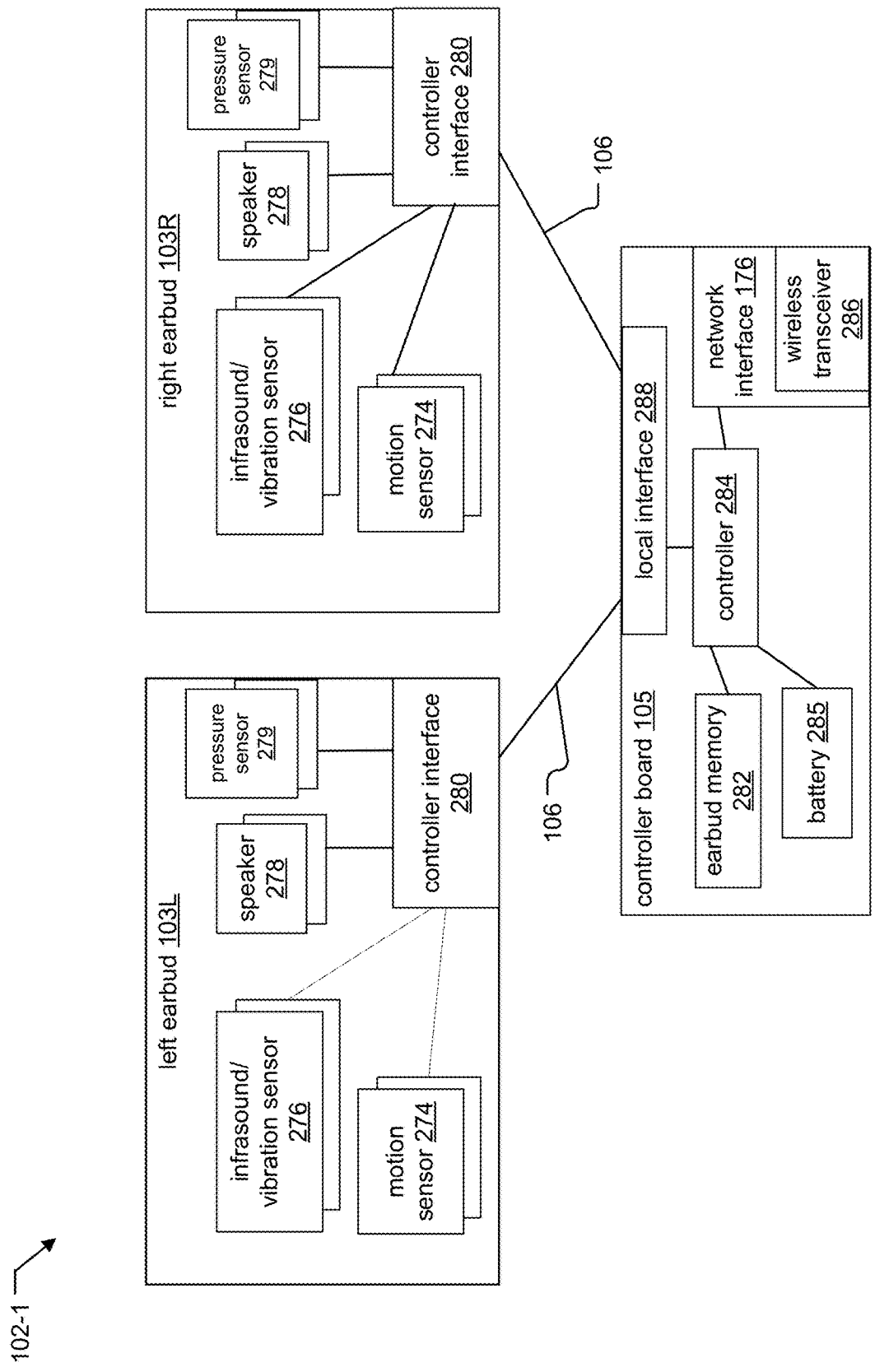
FIG. 6 is a schematic diagram showing detail for an implementation of the in-ear biosensor system in the cardiology systems of FIGS. 1, 3, and 5.

FIG. 6 shows detail for the in-ear biosensor system 102-1 in the cardiology systems 10 of FIGS. 1, 3, and 5.

The left and right earbuds 103L,103R include substantially the same components and operate in substantially the same way. The earbuds 103 each include one or more motion sensors 274, acoustic sensors such as infrasound/vibration sensors 276, speakers 278, pressure sensors 279, and a controller interface 280. The motion sensors include accelerometers and gyroscopes, in examples. The infrasonic/vibration sensors 276 operate in the infrasonic range, and might also operate in the audible range as well. The pressure sensors 279 can be used to characterize a level of seal/occlusion and monitor changes in baseline pressure in the ear-canal due to, for example, physiological changes. These pressure sensors 279 are examples of auxiliary sensors that can detect pressure biosignals in the individual's ear to monitor occlusion level of one or both of the earbuds 103L,R and to monitor physiological changes of the individual 100.

The controller board 105 includes a local interface 288, earbud memory 282, a battery 285, a controller 284, and a network interface 176. The network interface 176 further includes a wireless transceiver 286. The controller board 105 provides power to and enables communications between the earbuds 103L, 103R via the local interface 288 and the earbud connection 106.

Within the earbuds 103, the controller interface 280 connects to the sensors 274, 276 and the speakers 278. The controller interface 280 also connects to the controller board 105 via the earbud connection 106. In one implementation, the controller interface 280 is a wired bus.

Within the controller board 105, the controller 284 connects to local interface 288, the earbud memory 282, the battery 285, and the network interface 176. The controller 284 can be configured as a microcontroller or microprocessor. In one example, the controller 284 is a reprogrammable FPGA. The controller 284 controls the operation of the other components in the controller board 105.

The sensors 274, 276 within each of the earbuds 103L, 103R detect various information including sounds and vibrations originating from the individual 100 and send biosignals 101 representing the information to the controller board 105. These signals and vibrations are typically associated with operation of the heart and its various chambers and valves. Additionally, the sensors 276 can also detect sounds and vibrations associated with other cardiovascular components such as the lungs, and arteries, veins, coronary and portal vessels. The motion sensors 274 detect movement of the individual (e.g. moving, sneezing), and represent the motion as motion artifacts within the biosignals 101.

Infrasound refers to a range of sound signals that have a frequency below the frequency range of human hearing. Typically, infrasound signals are associated with sounds that are in the range of 0.01 Hertz (Hz) to 20 Hz. The frequency range of human hearing for a 20 year-old healthy adult, by contrast, is typically above 20 Hz but generally less than 18 KHz. In implementations, the infrasound/vibration sensors 276 can be configured to additionally detect some sounds above the typical range of infrasound, such as from 20 Hz to 25 Hz, or to additionally detect sounds over the entire audible range. In this way, these sensors 276 can detect some sounds associated with heart/cardiovascular activity above the infrasonic range that may augment the detection and analysis of heart rhythms and arrhythmias.

The controller board 105 receives the biosignals 101 sent from the earbuds 103 and transmits the biosignals 101 to other components in the system 10 via the network interface 176. The controller 284 receives the signals 101 from the earbuds 103 via the local interface 288, and buffers the signals in the earbud memory 282 or in local memory of the network interface 176. The network interface 176 then sends the biosignals 101 via the wireless transceiver 286 to other components of the cardiology system 10. Typically, the controller board 105 transmits the signals 101 to other components in the system 10, in response to receiving commands sent from the user app 40 executing on user device 107-1A worn by the individual 100.

The controller board 105 also receives information from other components in the system 10 via the network interface 176. This information includes the notification messages 111 for presentation at the earbuds 103L, 103R, and commands sent from the user app 40. In another example, the information includes updates for application code running within the controller 284. In yet another example, the information includes replacement image files for updating the internal logic of the controller 284 (when the controller is an FPGA). In still another example, the information includes requests to establish wireless communications links between the earbuds 103 and other components in the cardiology system 10.

It can also be appreciated that biosensor systems worn by the individual 100 other than the in-ear biosensor system 102-1 might be included within the cardiology system 10. In one example, patch biosensor system 102-4 that is removably attached to the skin near the heart might be employed. In another example, one or more biosensor systems that are removably attached to the skin near common pulse sites might be employed. These pulse sites might include the radial pulse (at the wrist below the thumb), apical pulse (chest), carotid pulse (neck), temporal pulse (palpated in front of the ear/near the temples), brachial pulse (located in a bend of either arm), and femoral pulse (front inside of leg near the crotch), in examples.

The patch biosensor systems typically include similar sensors and components as those shown in the in-ear biosensor system 102-1. In one implementation, the patch biosensor systems include the controller board 105 and a daughter board. The daughter board connects to the controller board by a wired or wireless connection 106. The daughter board generally includes the same sensors 274, 276, 279 and speakers 278 and controller interface 280 as one of the earbuds 103L/103R. In another implementation of the patch biosensor system, the sensors 274, 276, 279 and speakers 278 are included within the controller board 105. In this implementation, the controller interface 280 is not required and the sensors and speakers connect directly to and communicate over the local interface 288 of the controller board 105.

Figure 7:
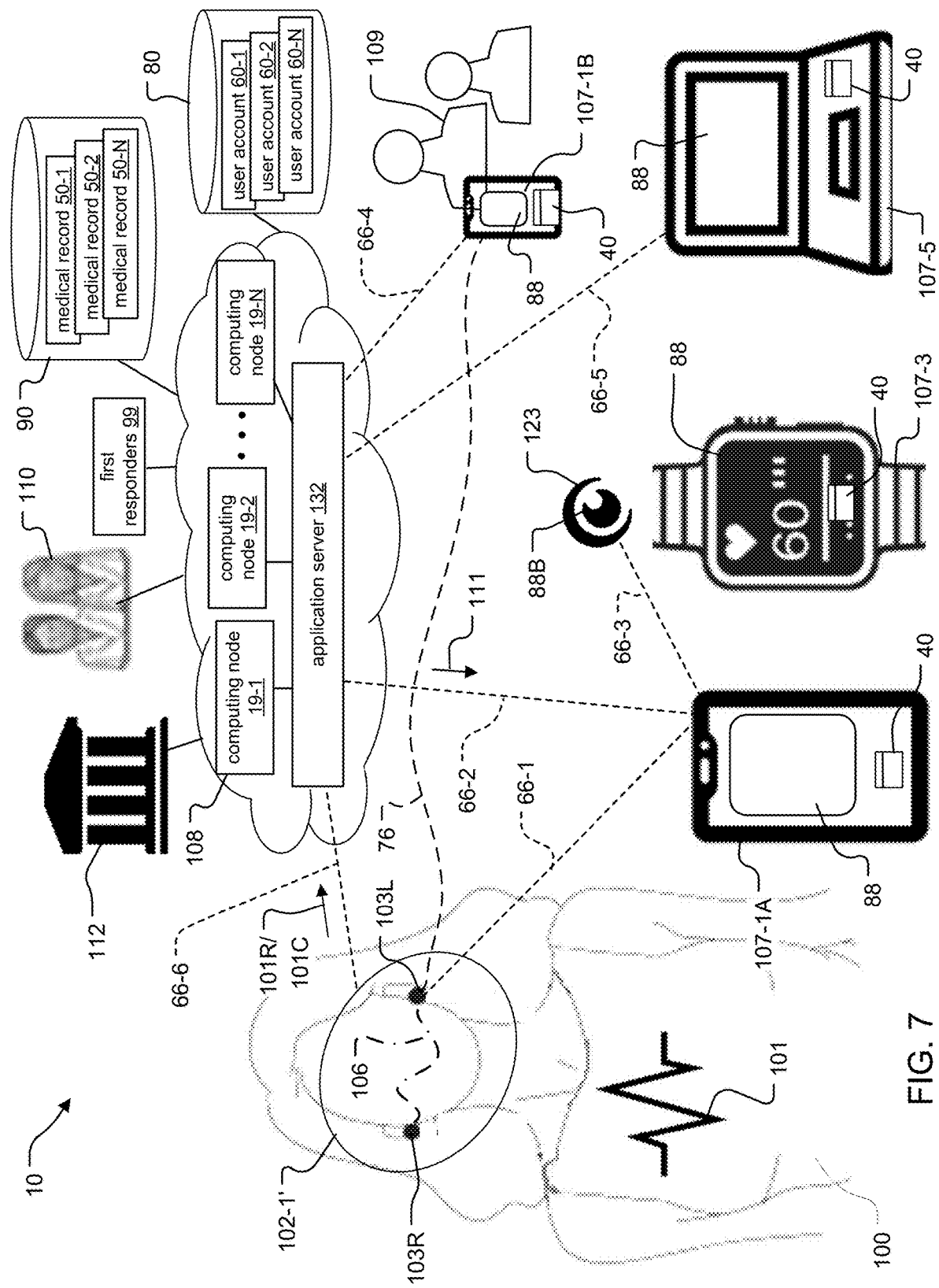
FIG. 7 is a schematic diagram of a cardiology system which is substantially similar to that shown in FIG. 1, but includes a different, all-wireless version of the in-ear biosensor system.

FIG. 7 is a cardiology system 10 that is substantially similar to that shown in FIG. 1. However, the system 10 includes an all-wireless version of the in-ear biosensor system, indicated by reference 102-1'.

In more detail, the in-ear biosensor system 102-1' includes a controller board 105 within each of the earbuds 103L, 103R. The earbuds 103L, 103R communicate with one another via their respective controller boards 105, and at least one of the controller boards 105 uses a wireless connection 66-6 to communicate with other components in the system 10. The wireless connection 66-6 supports the same wireless technologies as the connections 66-1 through 66-5, and also supports high-speed cellular 5G communications, in examples.

In the illustrated example, the individual 100 uses the user app 40 to establish an authenticated user session between the user device 107-1A and the application server 132. Once the individual 100 is authenticated, the user app 40 establishes wireless connection 66-1 between the user device 107-1A and at least one of the controller boards 105.

Then, the user device 107-1A sends commands over the wireless connection 66-1 to the at least one of the controller boards 105 of the in-ear biosensor system 102-1'. In one example, the commands instruct the in-ear biosensor system 102-1' to establish wireless connection 66-6 to the application server 132, and to send the biosignals (in either compressed or raw form 101C, 101R, respectively) over the wireless connection 66-6. The application server 132 then forwards the biosignals 101 to the cloud-based data analysis system 209 for analysis. In another implementation, the commands instruct the in-ear biosensor system 102-1' to establish wireless connection 66-6 with the cloud-based data analysis system 209, and to send the biosignals 101 over the wireless connection 66-6 to the data analysis system 209.

Figure 8:
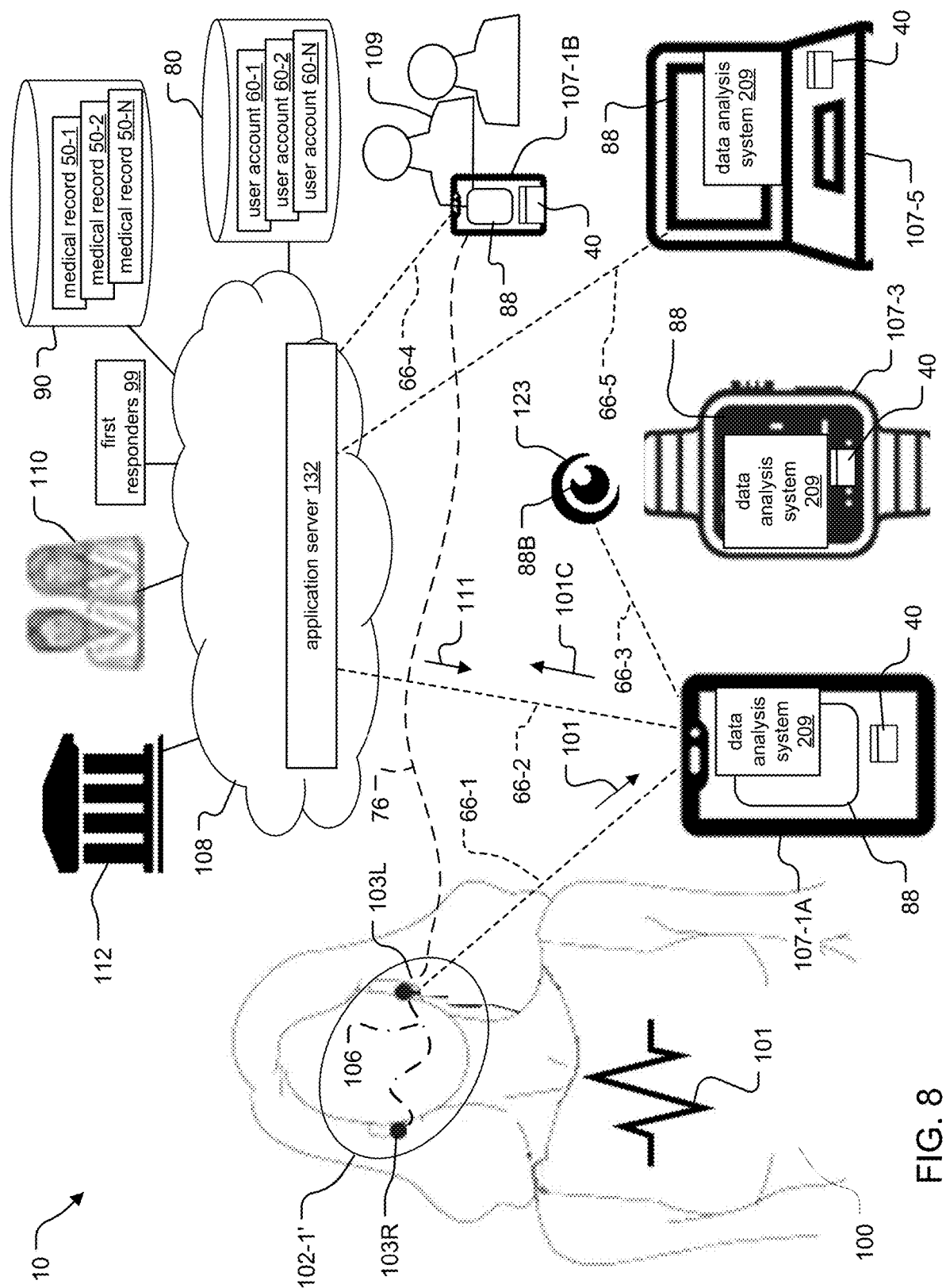
FIG. 8 is a schematic diagram of yet another exemplary cardiology system, where the data analysis system is distributed across multiple user devices and includes the all-wireless version of the in-ear biosensor system.

FIG. 8 shows yet another cardiology system 10. The system 10 includes the all-wireless in-ear biosensor system 102-1'. The data analysis system 209 is local to the user device 107-1A.

In the figure, after authenticating the individual 100, the user app 40 instructs the in-ear biosensor system 102-1' to send the biosignals 101 via wireless connection 66-1 to the user device 107-1A. Here, the wireless connection 66-1 might be a 5G cellular connection. Here, the data analysis system 209 local to user device 107-1A characterizes at least some of the biosignals 101 as being associated with cardiovascular activity, detects the heart rhythms from the signals 101, and carries out the classification of the arrhythmias, updating of medical records 50, and notification/reporting functions.

Figure 9:
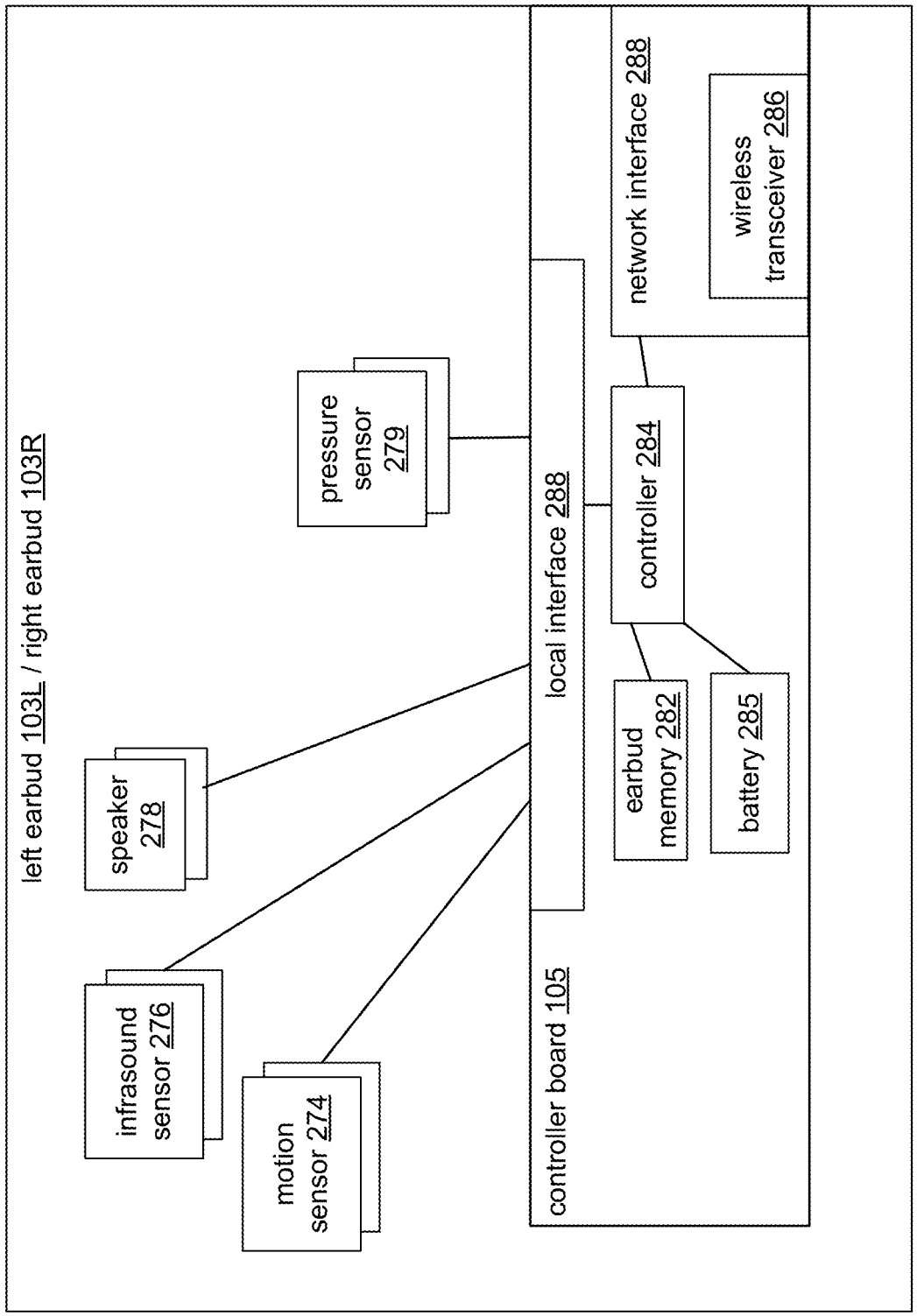
FIG. 9 is a schematic diagram showing detail for an implementation of the in-ear biosensor system in the cardiology systems of FIGS. 7 and 8.

FIG. 9 shows an implementation of the all-wireless in-ear biosensor system 102-1' in in the cardiology systems of FIG. 7 and FIG. 8. Both the left and right earbuds 103L, 103R have substantially the same components and are configured in substantially the same way.

Each of the earbuds 103L, 103R includes an instance of the controller board 105. Each controller board 105 is configured and has the same components as the controller board in FIG. 6. While the earbuds 103L, 103R communicate with each other via their controller boards 105, typically only one of the controller boards 105 is a "primary" controller for communicating externally with the other components of the cardiology system 10. This saves on power consumption. This primary controller buffers the biosignals 101 from each of the earbuds 103L, 103R for transmission to the external data analysis system 209.

Figure 10:
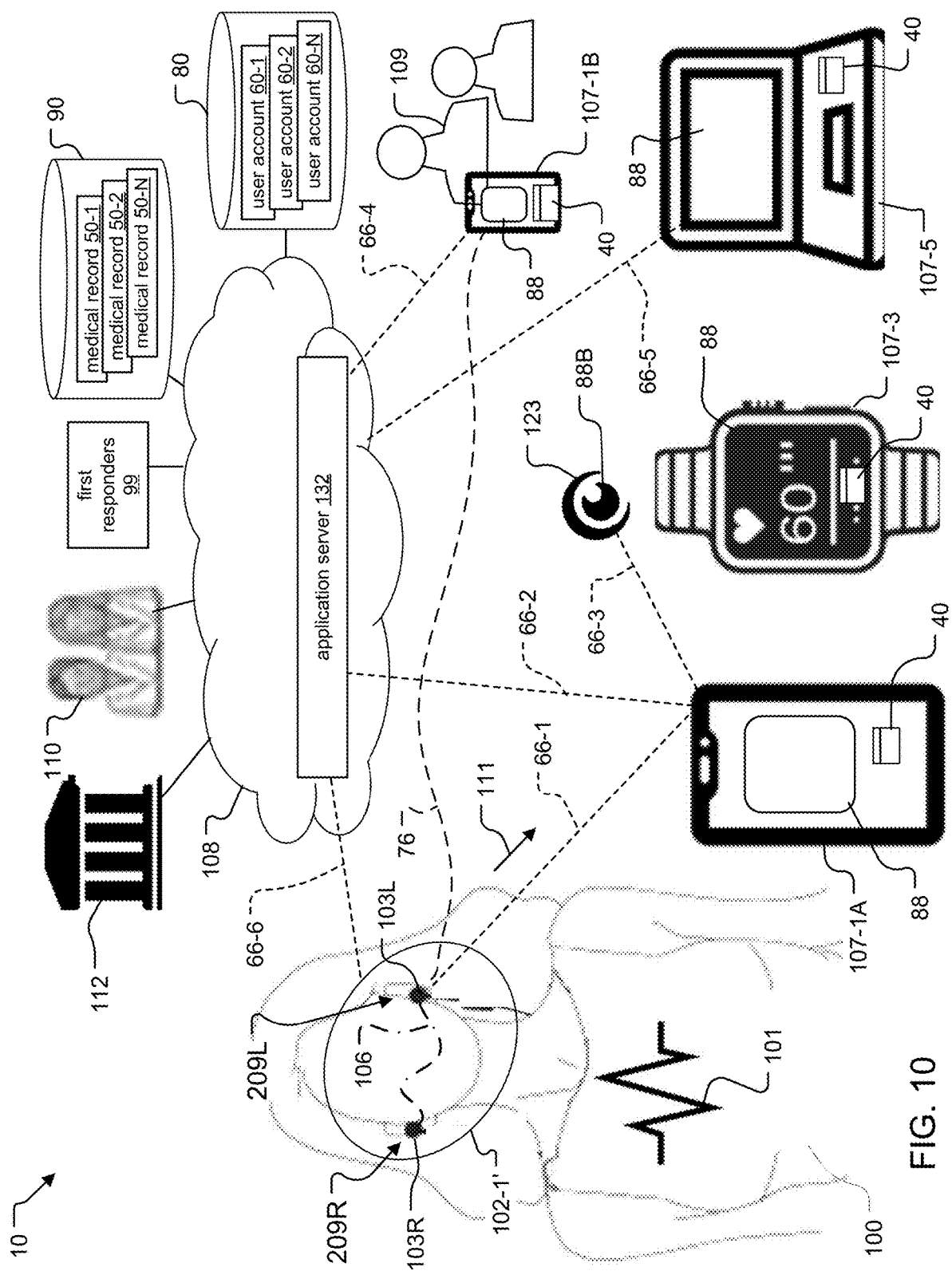
FIG. 10 is a schematic diagram of yet another exemplary cardiology system, where the data analysis system is located within the all-wireless version of the in-ear biosensor system.

FIG. 10 shows still another cardiology system 10. The system 10 includes the all-wireless version of the in-ear biosensor system 102-1'. In addition, at least one or possibly both of the earbuds 103L, 103R includes an instance of the data analysis system 209. Here, earbud 103L includes data analysis system 209L and earbud 103R includes data analysis system 209R. In this way, the cardiology system 10 of FIG. 10 can determine heart rhythms of the individual 100 from the biosignals 101, at the level of the earbuds 103.

Figure 11:
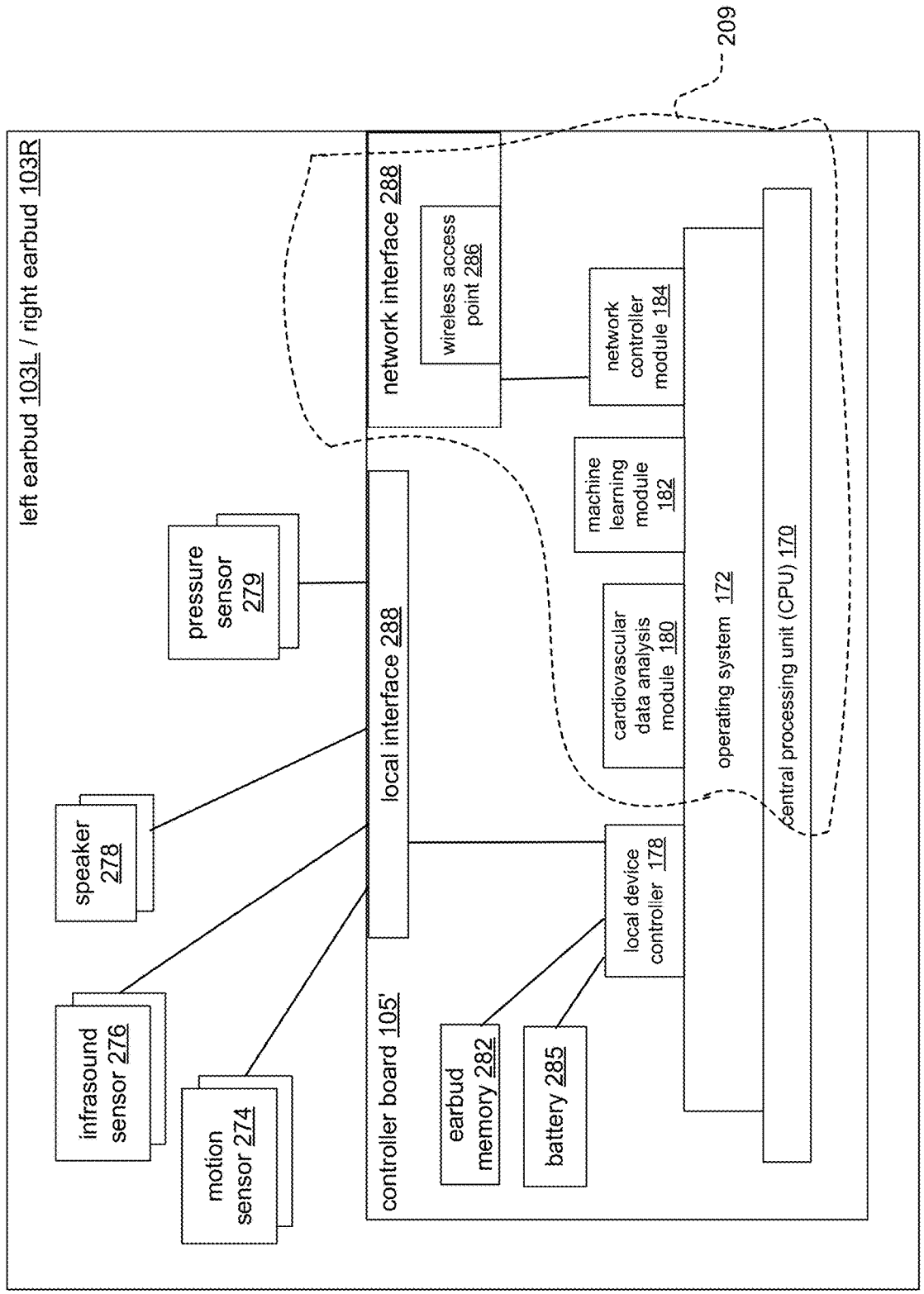
FIG. 11 is a schematic diagram showing detail for an implementation of the in-ear biosensor system in the cardiology system of FIG. 10.

FIG. 11 shows more detail for the in-ear biosensor system 102-1' in FIG. 10. In the figure, each of the earbuds 103L, 103R includes an instance of controller board 105', and one of the controller boards acts as a primary controller board for communicating with components external to the in-ear biosensor system 102-1'.

The controller board 105' within each of the earbuds 103L, 103R is configured as a microprocessor. Specifically, the controller board 105' includes the same components as the computing nodes 19 of the data analysis system 209 in FIG. 2A. However, each controller board 105' includes additional components, and operates in a somewhat different manner.

Each controller board 105' additionally includes a local device controller 178 module on top of the operating system 178, a local interface 288, a battery 285 and an earbud memory 282. Within the controller board 105', the local interface 288 connects to the battery 285 and the earbud memory 282. The local interface 288 also connects to and controls the motion sensors 274, the infrasound/vibration sensors 276, the speakers 278, and pressure sensor 279. The data analysis system 209 formed within the controller board 105' includes the same components as in the data analysis systems 209 described hereinabove.

Returning to FIG. 11, after authenticating the individual 100, the user app 40 commands/instructs the in-ear biosensor system 102-1' to send the biosignals 101 to a data analysis system 209 for analysis. The primary controller 105' receives the command, and application code executing on the CPU 170 indicates that at least one local data analysis system 209L/R exists. The primary controller 105' then instructs the local data analysis system 209L/209R to characterize at least some of the biosignals 101 as being associated with cardiovascular activity and analyzes the signals 101. The local data analysis system 209L/209R also carries out the classification of the arrhythmias, updating of medical records 50, and performs the various notification/reporting functions.

Figure 12:
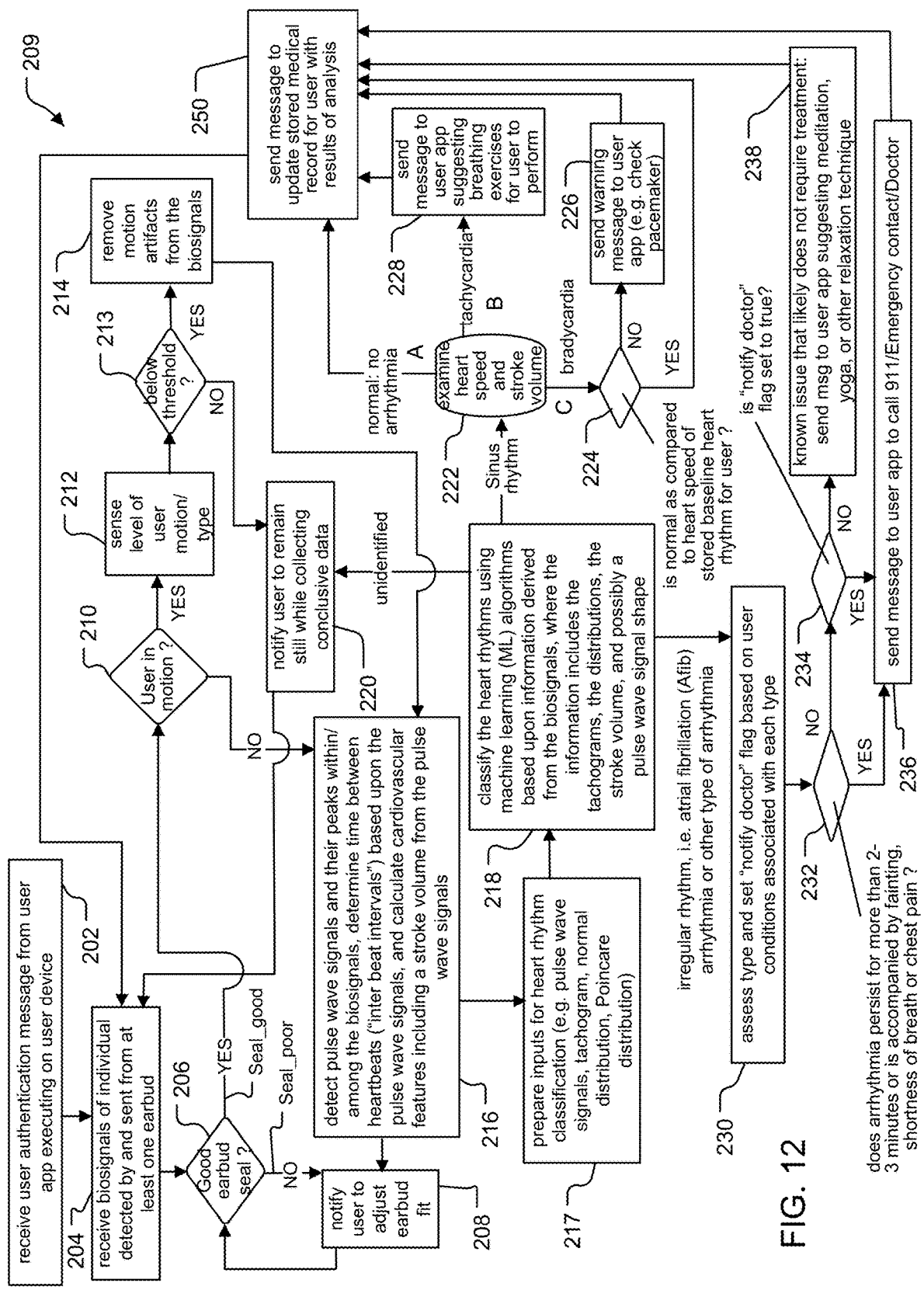
FIG. 12 is a flow diagram that describes a method of operation of the data analysis system in the various cardiology systems listed hereinabove, where the method describes how the data analysis system detects, classifies, and reports heart rhythms and arrhythmias from biosignals of the individual.

FIG. 12 is a flow diagram that describes a method of operation of the data analysis system 209 in the cardiology systems 10 listed hereinabove. Various steps in the method are described/illustrated by the remaining figures, duly noted in various particulars hereinbelow. While this flow diagram uses the in-ear biosensor system 102-1 to illustrate operation of the method, it can be appreciated that any of the patch biosensor systems referenced and described hereinabove could also be used.

In step 202, the network interface module 184 of the data analysis system 209 receives a user authentication message from the user app 40 executing on a user device 107, such as user device 107-1A. This message indicates that the individual 100 is an authorized user of the cardiology system 10, and the execution of the method proceeds to step 204.

In step 204, the network interface module 184 receives biosignals 101 from the earbuds 103L, 103R of the in-ear biosensor system 102-1 and forwards the signals 101 to the cardiovascular data analysis module ("analysis module") 180 for analysis. The system can also send signals from auxiliary sensors such as motion sensor 274 and pressure sensor 279. According to step 206, the analysis module 108 determines whether the earbuds 103L, 103R are snugly fit in the ear canals of the individual 100. Signals from the earbuds 103L, 103R have a low signal amplitude when the earbuds 103L, 103R are improperly placed within the ears of the individual 100. The signals from auxiliary sensors 274 and 279 can also be used to help assess seal level (i.e. occlusion level of the at least one earbud in the ear canal). When the biosensor systems are the patch biosensor systems, the assessment of the seal level indicates whether a proper seal of the patch/gel/skin exists.

Figure 13A:
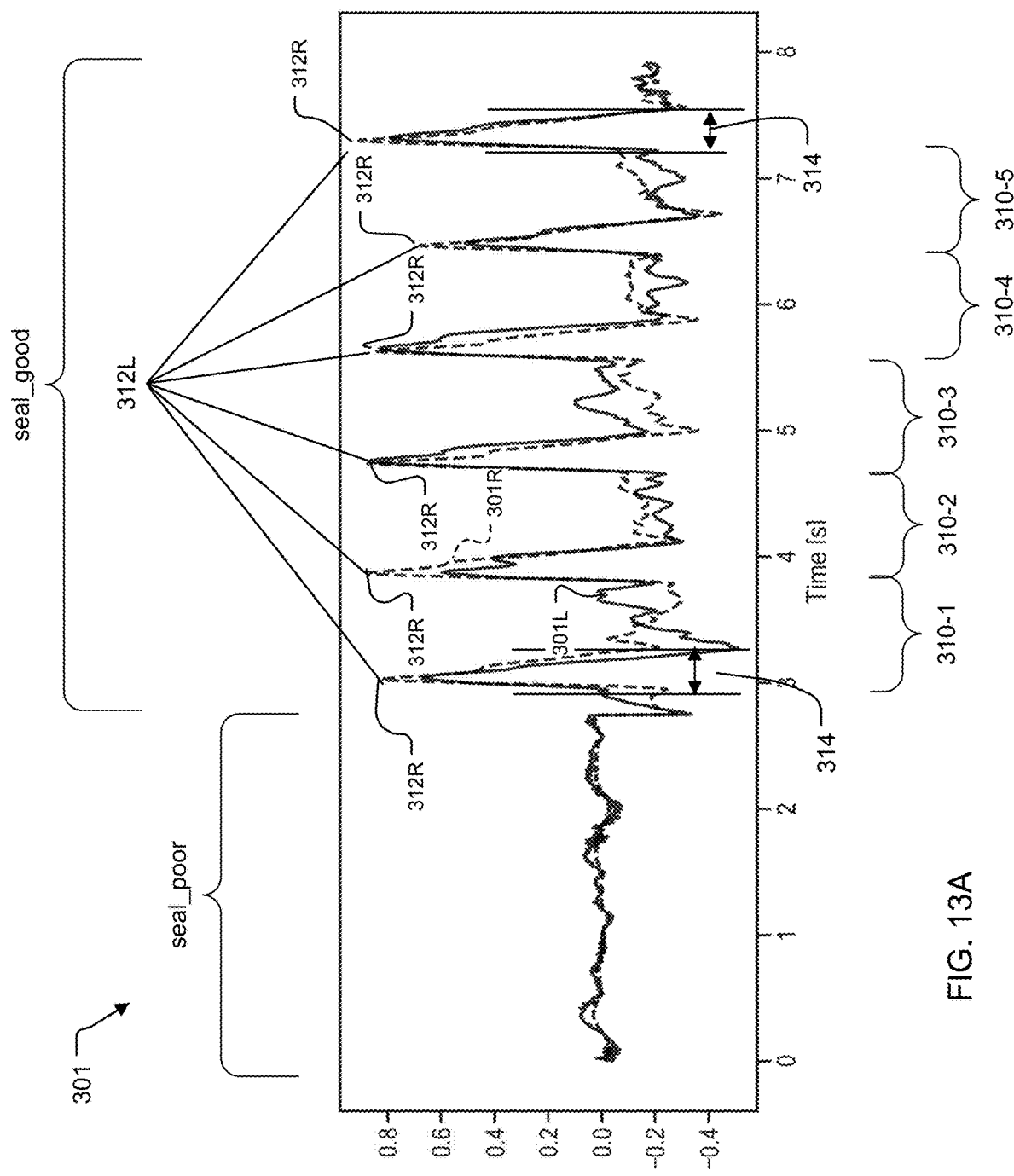
FIG. 13A is an amplitude versus time plot of pulse wave biosignals (pulse wave signals) of an individual determined in accordance with the method of FIG. 12, where pulse wave signals obtained by the left and right earbuds are shown over a small number of consecutive heart cycles.

FIG. 13A shows an exemplary amplitude versus time plot of biosignals 101 characterized as being associated with cardiac activity by the data analysis module 108. The biosignals 101 are pulse wave signals 301 with a peak corresponding to systole peak signals ("pulse wave peak") 312 and possibly and other cardiovascular events such as mitral valve closing, aortic valve opening and aortic valve closure timing signals among others that are obtained by the left and right earbuds 103L, 103R.

The biosignals 101 were detected by at least one infrasound/vibration sensor 276 and/or pressure sensor 279 of each earbud 103L, 103R. The earbuds 103L,R are respectively positioned inside and/or at the left and right ear canals of the individual 100. In examples, the infrasound/vibration sensors 276 are microphones or other transducers that convert infrasound and/or audible signals and vibrations to a corresponding voltage signal.

Five heart cycles 310-1 through 310-5 of the biosignals 101 are shown. Each heart cycle 310 includes a prominent pulse wave signal 301 of the biosignals 101 with a peak 312. In more detail, each pulse wave signal 301 is a composite of a left pulse wave signal 301L obtained by the left earbud 103L, and a right pulse wave signal 301R obtained by the right earbud 103R. Peaks 312L, 312R of the left and right pulse wave signals 301L, 301R are also shown.

Within each heart cycle 310, each leading peak 312 follows ventricular depolarization and traces its associated pulse wave signal 301. In this way, the pulse wave signals 301 provide information directly related to the mechanical change in the cardiovascular cycle related to blood flow, blood pressure, and viscosity, in examples. As a consequence, the pulse wave signals 301 over time (and information derived from the pulse wave signals 301) can be used to calculate or estimate, for example, cardiovascular output and other information that is not accessible with the Apple Watch device or the existing medical diagnostics systems, including the ECG systems. Thus, the system 10 can determine heart rhythms of the individuals 100 based upon the pulse wave signals 301 and detect whether the rhythms are associated with arrhythmias, in particular Afib arrhythmias. Also, information derived from the pulse wave signals 301 can be used to further classify the arrhythmias and can improve heart arrhythmia detection and categorization as compared to the existing medical diagnostics systems and the Apple Watch device, in examples.

Reference "seal_poor" shows the near-zero amplitude of and lack of information within the pulse wave signals 301 when the earbuds 103 are improperly positioned/fit within the ear canals of the individual 100. In a similar fashion, reference "seal_good" shows exemplary pulse wave signals 301 when a proper fit/seal of the earbuds 103 exists.

Heart cycles 310-1 through 310-5 of the biosignals 101/ pulse wave signals 301 are shown. Here, the individual 100 is stationary. During this time, the pulse wave signals 301 are substantially similar in both amplitude and wavelength across the heart cycles 310-1 through 310-5.

Returning to FIG. 12 step 206, the method transitions to step 208 when the earbud seal is improper. The analysis module 108 sends a message via the network interface module 184/network interface 176 to the user app 40. The message instructs the individual 100 to adjust the fit of the earbuds 103L, 103R, and the method transitions back to step 206 to re-evaluate the seal of the earbuds 103. If the seal is proper, the method transitions to step 210.

According to step 210, the analysis module 180 determines whether the individual 100 is in motion based upon the biosignals 101 (here, the pulse wave signals 301). If no motion is detected, the method transitions to step 216. Otherwise, the method transitions to step 212 to sense the level of user motion, and what type. The motion can be also be assessed using biosignals 101 detected by the auxiliary motion 274 and pressure sensors 279. Here, the module 180 can detect changes in the baseline pressure in the individual's ear canal from the biosignals 101 to assess motion of the individual 100.

Figure 13B:
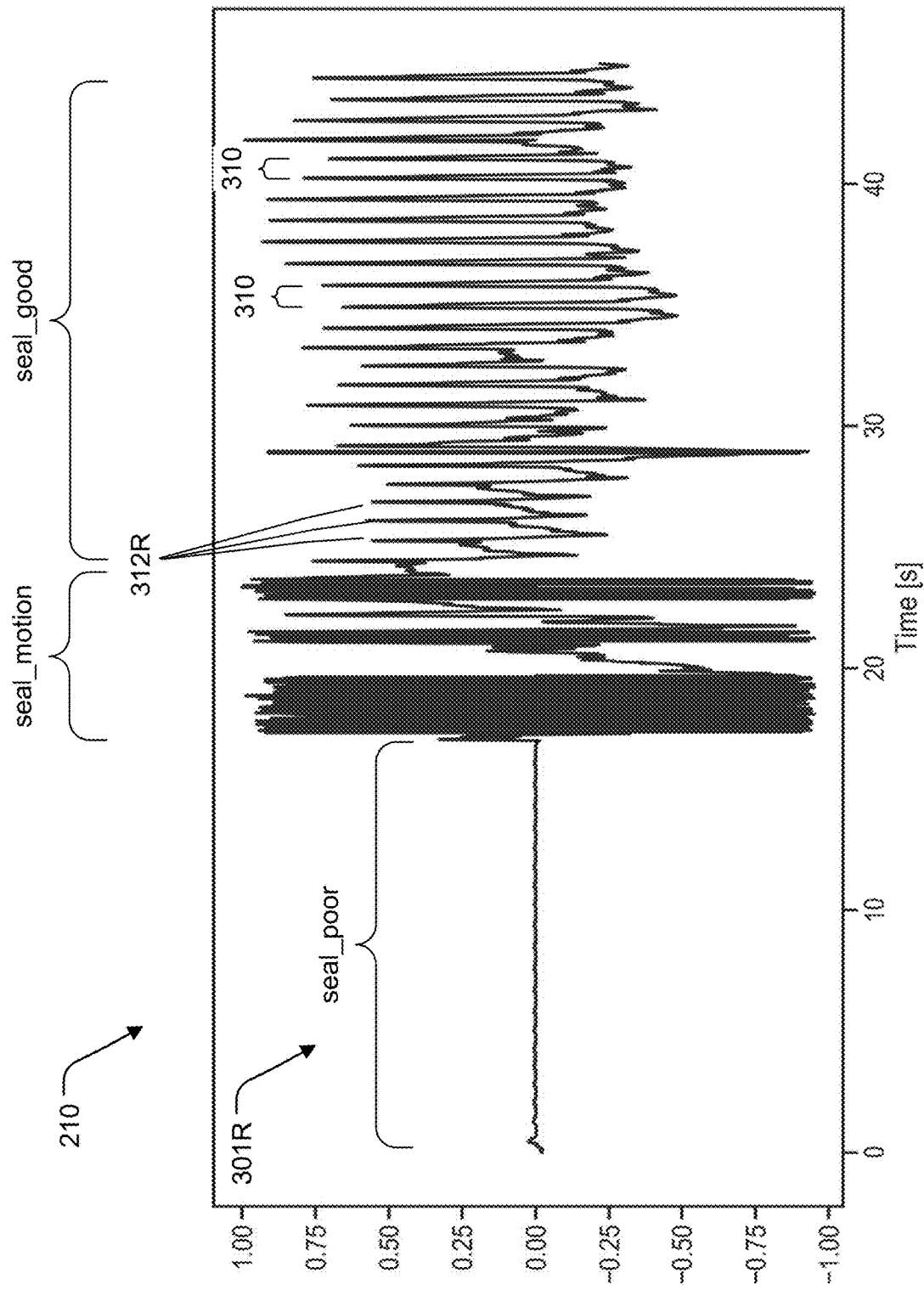
FIG. 13B is a single-channel plot of pulse wave signals detected in accordance with the method of FIG. 12, where the plot illustrates how the method can filter motion artifacts from the pulse wave signals.

FIG. 13B is a plot of pulse wave signals 301R. Here, the pulse wave signals 301R are from only the right earbud 103R. The plot shows both the effect of fit/seal of the earbuds 103 upon the pulse wave signals 301R and motion of the individual 100 superimposed upon the pulse wave signals 301R. The plot also illustrates the operation of method step 210 in FIG. 12.

Reference "seal_poor" shows the near-zero amplitude of and apparent lack of visible information within the pulse wave signals 301R and their peaks 312R. This occurs when the earbud 103R is improperly positioned/fit within the ear canal of the individual's right ear. In a similar fashion, reference "seal_good" shows the pulse wave signals 301R and peaks 312R for a proper fit. Finally, reference "seal_motion" shows motion artifacts introduced into the pulse wave signal 301R when the earbud 103R has a proper fit and the individual 100 is moving/not at rest.

It is important to note that detection of pulse wave signals 301L,R from the earbuds 103L, 103R in both ears helps reject noise and spurious peaks, providing results of higher quality. Differences detected in the biosignals 101 from the left and right earbuds 103L,R can be used to improve a signal to noise ratio of the biosignals 101.

Returning to FIG. 12 step 212, the analysis module 180 detects motion artifacts within the biosignals 101, and senses a level (e.g. amplitude) and possibly a type. In step 213, the analysis module 180 compares the motion level to a predefined motion threshold to determine whether the motion can be removed (i.e. filtered) from the biosignals 101. In another example, the analysis module 180 might determine whether the motion can be removed based on its type, such as motion characteristic of sneezing as opposed to running or jumping, in examples. If the motion is below the threshold, the method transitions to step 214 and the analysis module 180 removes (e.g. by deconvolution/Wiener filtering) the motion artifacts from the biosignals 101. The method then transitions to step 216. If the motion level is above the threshold, however, new biosignals 101 without motion artifacts must be obtained, and the method transitions to step 220. As a result, the data analysis system 209 can identify and remove motion artifacts associated with motion of the individual 100 from the biosignals 101 prior to determining the heart rhythms of the individual 100.

According to step 220, the analysis module 180 notifies the individual 100 to remain still during the analysis/while collecting conclusive biosignals 101. The method then transitions to step 204, and the network interface module 184 waits for new biosignals 101 from the earbuds 103.

In step 216, the analysis module 180 detects the pulse wave signals 301 and their peaks 312 within/among the biosignals 101, determines time between heartbeats ("inter beat intervals") based upon the pulse wave signals 301/pulse wave peaks 312, and calculates cardiovascular features such as a stroke volume from the pulse wave signals 301.

Several algorithms can be used for detection of pulse wave signals 301/pulse wave peaks 312. In one implementation, peaks 312 are detected using reference criteria based on peak amplitudes and minimum time between successive peaks. The minimum expected time between peaks can be estimated as a fraction of the averaged inter beat intervals 320. Averaged inter beat intervals can be calculated from autocorrelation functions, Fourier transforms of the biosignals 101, or by multiple peak-detection passes, where the first pass is performed using only criteria based on peak amplitudes. The peak detection is typically performed within short (2-10 second) time windows or segments. The robustness of this method can be improved with an additional requirement of the same biosignal peaks being identified in multiple sliding time windows. In another implementation, biosignal peaks are identified as part of time-series models, e.g., generalized additive models, autoregressive models, or models based on theoretical, simulation, or physics-based representations of the biosignals 101.

Figure 14:
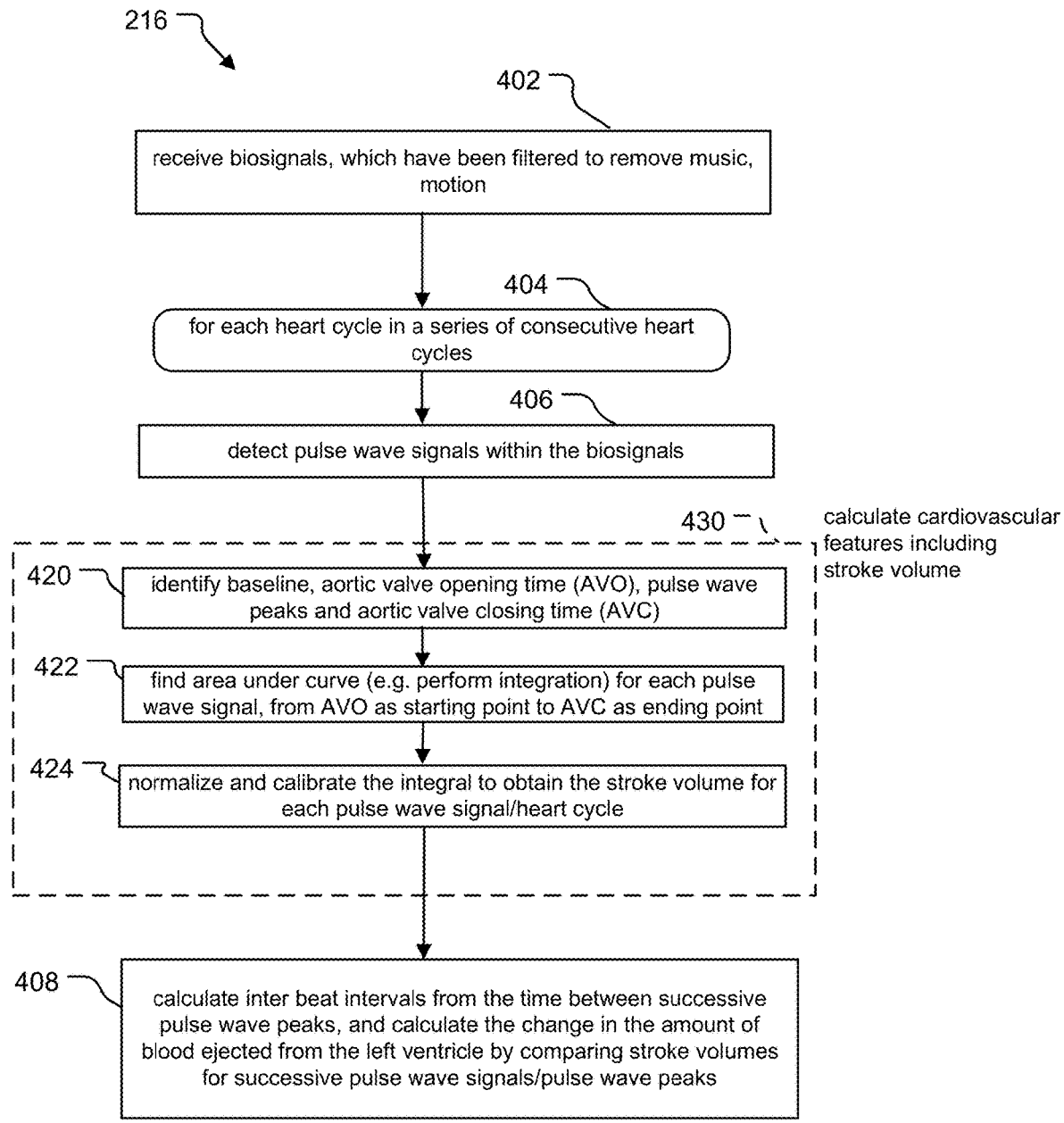
FIG. 14 is a flow chart that shows more detail for analysis of biosensor signals in the method of FIG. 12.

FIG. 14 is a flow chart that describes step 216 of FIG. 12 in more detail.

In step 402, the analysis module 180 receives the biosignals 101, which have been filtered to remove motion and/or music. Then, in step 404, for each heart cycle 310 in a series of consecutive heart cycles 310, the analysis module 180 carries out steps 406, 430, and 408 in succession. According to step 406, the analysis module 180 detects the pulse wave signals 301 within the biosignals 101.

FIG. 15A through 15C are plots of pulse wave signals 301 for the same individual 100, detected in accordance with the method of FIG. 12. Specifically, FIGS. 15A and 15B are single-channel plots of pulse wave signals 301 obtained by the right and the left earbuds 103R, 103L, respectively, and FIG. 15C combines the plots of FIGS. 15A and 15B. In FIGS. 15A and 15B, skipped beats 806R, 806L and extra beats 804R, 804L are shown. Inter beat intervals 320 are also shown.

FIG. 15D shows pulse wave signals 301 for a healthy individual 100 with regular/sinus heart rhythms. Only one channel of the pulse wave signals 301R, from the right earbud 103R is shown. Times between inter beat intervals 320 are clearly visible.

FIG. 15E shows exemplary pulse wave signals 301 from an individual diagnosed with atrial fibrillation. Only one channel of the pulse wave signals 301L, from the left earbud 103L is shown. The illustrated example shows that the cardiology system 10 can clearly detect irregular inter beat intervals/heart rhythms from the pulse wave signals 301L. In contrast, FIG. 15F shows pulse wave signals 301 and peaks 312 for regular heart rhythms detected using both right and left earbuds 103 of the cardiology system 10.

The illustrated examples provided by FIGS. 15A-15C and 15F also show the "stereo" benefit of the earbuds 103L, 103R. Specifically, the earbuds 103L, 103R detect the biosignals 101 such as the pulse wave signals 301L, 301R at substantially the same time from two different "channels" (from both the left and the right ear). Noise, artifacts or other spurious data within the signals from one of the channels may not be present in the other. As a result, when the information is received at the data analysis system 209, the software/firmware modules such as the analysis system 180 can compare the individual components 301L, 301R of the composite pulse wave signals 301. In this way, the data analysis system 209 can reject spurious data that is present in locations in one pulse wave signal/channel 301L that is not present in the same locations in the other channel 301R.

Returning to the method of FIG. 14, the method then transitions to step 430. In step 430, the analysis module 180 calculates cardiovascular features based upon the pulse wave signals, including a stroke volume under each of the pulse wave signals 301.

During an arrhythmia, the amount of blood ejected by the heart decreases. This is due to a problem with the heart that limits its ability to contract and send sufficient blood flow (and thus oxygen) to the cells of the body. The decrease in blood ejected from the heart causes health risks such as shortness of breath and fatigue, in examples.

The stroke volume and other cardiac events such as left ventricular ejection time provide an indication of how efficiently the heart is pumping blood. Specifically, the stroke volume measures the amount of blood ejected from the ventricles (in particular, from the left ventricle) during a given heartbeat/ventricular contraction. By monitoring the stroke volume over time, the system 10 can determine whether the heart efficiency for pumping blood has dropped, and can identify, classify and recognize unhealthy heart arrhythmias. Thus, one of the ways of detecting arrhythmias (and also to classify the arrhythmias, especially unhealthy ones) is by calculating and monitoring the stroke volume over time.

Figure 16:
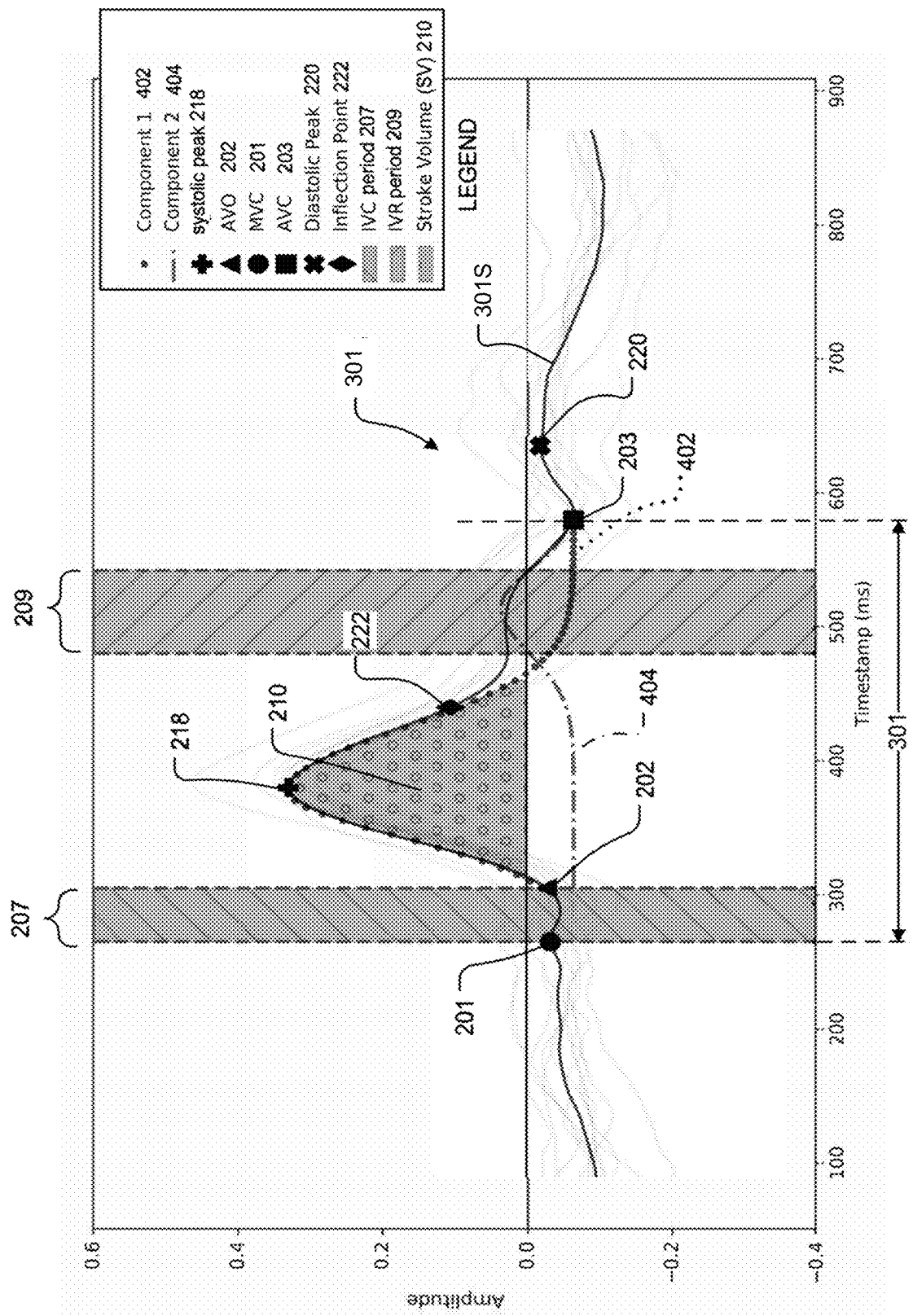
FIG. 16 is a single-channel plot of multiple pulse wave signals "stacked" or averaged, where the plot illustrates how the method of FIG. 14 can calculate cardiovascular features including a stroke volume from the pulse wave signals.

FIG. 16 illustrates calculation of cardiovascular features including the stroke volume from the pulse wave signals 301, in step 430 of FIG. 14. In the illustrated example, multiple pulse wave signals 301 and their stacked or averaged signal 301S are plotted over time.

The analysis module 108 can calculate various cardiovascular features from the pulse wave signals 301. These features include a baseline signal, a systolic peak 218, an aortic valve opening time (AVO) 202, a mitral valve closing time (MVC) 201, an aortic valve closing time (AVC) 203, a diastolic peak 220, and an inflection point 222, in examples. Additional features include an isovolumetric contraction period (IVC) 207, an isovolumetric relaxation period (IVR) 209, and stroke volume 210, and possibly even an overall shape of the pulse wave signal 301.

The baseline signal is the value of the pulse wave signal 301 when no measurable variation is detected by the infrasound/vibration sensor 216. The systolic peak 218 is the same as the value of the pulse wave peak 312.

The overall shape of the pulse wave signal 301 can be determined in various ways. In one example, the shape can be determined via analytical functions with at least two components 402 and 404 that represent the forward and reflected pulse waves, respectively. Additionally, the shape could be determined using templates from biosignal simulations, or within comprehensive time-series models, e.g., generalized additive models, autoregressive models, and recurrent neural networks, in examples.

Returning to FIG. 14 step 430, the calculation of the stroke volume 210 is accomplished via steps 420, 422, and 424. In step 420, the analysis module 180 identifies the baseline signal, AVO 202, pulse wave peaks 312 and the AVC 203. According to step 422, the analysis module 180 calculates the area under the curve of the pulse wave signal 301 (e.g. by performing integration) from the AVO 202 as a starting point to the AVC 203 as the ending point. Because the time interval between the AVO 202 to the AVC 203 is within the systole, the stroke volume 210 of each pulse wave signal 301 can thus be calculated by integrating each pulse wave signal during the systole period.

In step 424, the analysis module 180 normalizes and calibrates the integral to obtain the stroke volume 210 for each pulse wave signal 301/heart cycle 310. The method then transitions to step 408.

In step 408, the analysis module 180 calculates inter beat intervals from the times between successive pulse wave peaks 312, and calculates the change in the amount of blood ejected from the left ventricle by comparing stroke volumes for successive pulse wave signals 310/pulse wave peaks 312.

As a result, the data analysis system 209 determines heart rhythms of the individual 100 based upon the biosignals 101 by detecting pulse wave signals 301 in the biosignals, calculating stroke volumes 210 under each of the pulse wave signals 301 during systole times, and computing the heart rhythms from changes in the stroke volumes.

Upon completion of step 408, control passes back to FIG. 12, at the completion of step 216.

Returning to FIG. 12, in step 217, the method prepares inputs for heart rhythm classification (e.g. pulse wave signals, tachogram, normal distribution, Poincare distribution). The method can also compare the left ventricular ejection time, isovolumetric contraction time, or duration of the forward and backward waves in the consecutive peaks.

The current state of the art for detecting arrhythmias is the ECG medical diagnostics system, which measures the time between heartbeats in the form of RR intervals within the ECG. However, unlike the cardiology system 10, the existing ECG medical diagnostics systems do not have capability to measure stroke volume, or other cardiovascular features like the AVO 202 and AVC 203, which are used to derive the systole/left ventricular ejection time. As such, the ability of the existing ECG medical diagnostics systems to assess overall cardiovascular health is more limited as compared to the cardiology system 10.

FIG. 17A and FIG. 17B illustrate step 217 of FIG. 12.

FIG. 17A is a single-channel plot of pulse wave signals 301 of an individual 100 detected in accordance with the method of FIG. 12. By comparison, FIG. 17B is an ECG plot of heart operation of the same individual 100, obtained by standard ECG medical diagnosis equipment. Here, the individual 100 was the subject of both testing methods at substantially the same time and over substantially the same duration.

In more detail, FIG. 17A shows pulse wave signals 301 over five heart cycles 310. The analysis module 180 calculates the inter beat intervals 320 based upon the pulse wave signals 301. Specifically, the inter beat intervals 320 are the time intervals between successive pulse wave signal peaks 312. The interval between the aortic valve opening time (AVO) and the aortic valve closing time (AVC) is also shown. This interval is known as a left ventricular ejection time (LVET) 314.

In FIG. 17B, RR intervals within the ECG plot are shown. The RR intervals are periods between R peaks in successive QRS complexes within the ECG. The RR intervals are virtually identical in duration to the inter beat intervals times 320 in FIG. 17A. Also within the ECG, P and T waves are identified.

Figure 18:
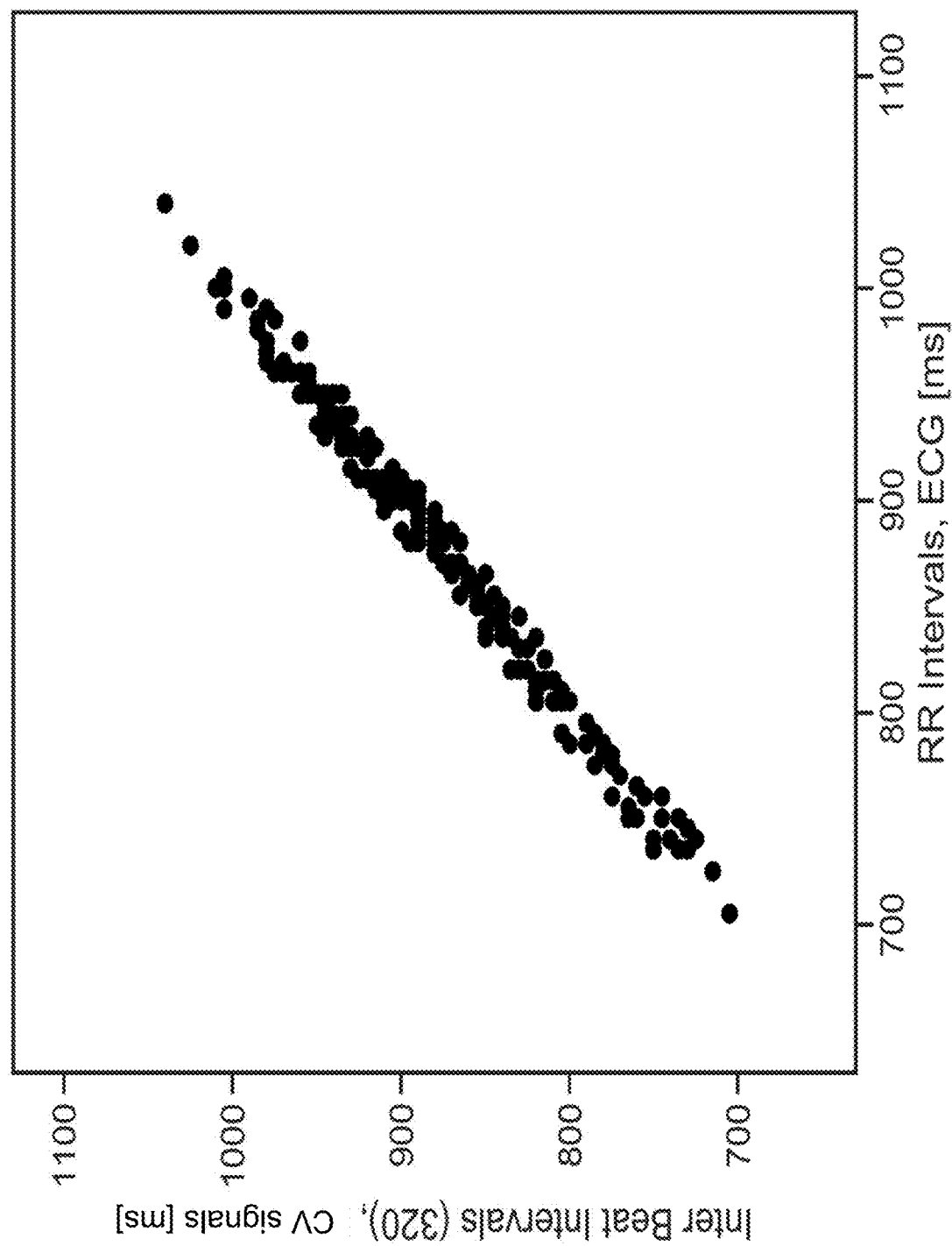
FIG. 18 is a graph of inter beat intervals versus RR intervals, where the inter beat intervals are from data within the pulse wave signals of FIG. 17A and are plotted against the RR intervals from data within the ECG plot of FIG. 17B, and where the graph shows a strong correlation between the information obtained by the cardiology system and the ECG system for the same individual.

FIG. 18 further illustrates step 217 in FIG. 12. Specifically, the figure shows how closely the inter beat intervals 320 calculated by the cardiology system 10 in FIG. 17A match and track the RR intervals of the ECG system in FIG. 17B for the same individual 100. For this purpose, the figure plots the inter beat intervals times 320 against the RR intervals. The strong linear nature of the graph indicates a strong correlation between the inter beat intervals 320 computed by the cardiology system 10 and the RR intervals computed by the ECG system.

Returning to the method of FIG. 12, step 217, the analysis module 180 can determine the heart rhythm of the individual from the inter beat intervals 320 and/or from the stroke volume 210 using various methods (e.g. tachogram, normal distribution, Poincare distribution).

FIGS. 19A and 19B illustrate how the analysis module 180 determines the heart rhythm of a healthy individual 100 from the inter beat intervals 320 of the biosignals 101/pulse wave signals 301.

In more detail, FIG. 19A shows about 57 pulse wave signals 301L and associated pulse wave peaks 312L associated with only one of the earbuds 103L. The pulse wave signals 301L and peaks 312L are determined in accordance with the method of FIG. 12 and are obtained and plotted over a period of at least 50 seconds. The analysis module 180 then determines the inter beat intervals from the pulse wave peaks 312.

In FIG. 19B, the analysis module 180 plots a tachogram of the inter beat intervals in FIG. 19A as another way to obtain the heart rhythms 500-1 of the healthy individual 100. Specifically, the pulse wave peaks 312 from FIG. 19A are plotted over time and normalized over a 60-second period to form the tachogram.

FIG. 19B also shows lines indicating one, two, and three standard deviations above and below the average of inter beat intervals. In the illustrated example, the heart rhythms 500-1 are sinusoidal in nature, and the inter beat intervals are usually limited to no more than one standard deviation above or below the average.

A non-exhaustive list of features that are derived from the tachogram and computed from inter beat intervals used for distinguishing between sinus rhythms and heart arrhythmias include: standard parameters of IBI distribution, mean/median absolute deviation, and coefficient of variance, defined as the ratio of standard deviation and the mean. Other features include a root mean square of successive inter beat intervals (RMSSD), entropy measures (e.g., sample entropy, Shannon entropy), turning point ratio, pNNx-fraction of signal segment during which the change in successive IBI exceeds x, and IBI power spectrum features (e.g., power or ratio of powers for different ranges in the power spectrum, power spectrum slopes).

In this way, the analysis module 180 can determine the heart rhythms 500-1 of the individual 100 based upon the biosignals 101 by detecting pulse wave signals 301 in the biosignals, determining inter beat intervals 320 of the heart based upon the pulse wave signals 301, and computing the heart rhythms from the inter beat intervals 320. In the illustrated example, outliers 510 in the plot are also shown.

FIGS. 20A and 20B illustrate how the analysis module 180 determines the heart rhythm 500-2 of an unhealthy individual 100 diagnosed with Afib from the inter beat intervals 320 of the biosignals 101/pulse wave signals 301.

In more detail, FIG. 20A shows about 45 pulse wave signals 301L and associated peaks 312L associated with only one of the earbuds 103L. The pulse wave signals 301L and peaks 312L are determined in accordance with the method of FIG. 12 and are obtained and plotted over a period of at least 50 seconds. The analysis module 180 then determines the inter beat intervals from the pulse wave peaks 312.

In FIG. 20B, the analysis module 180 plots a tachogram of the inter beat intervals in FIG. 20A to obtain the heart rhythms 500-2 of the unhealthy individual 100 with diagnosed Afib. Specifically, the pulse wave peaks 312 from FIG. 20A are plotted over time and normalized over a 60-second period to form the tachogram. In this way, the analysis module 180 can determine the heart rhythm 500-2 of the unhealthy individual 100 from the inter beat intervals 320.

As in the tachogram for the healthy individual 100 in FIG. 19B, the tachogram for the individual experiencing Afib in FIG. 20B has outliers 510 in the plot, and the inter beat intervals are provided over 3 upper and lower standard deviations. Unlike the tachogram of FIG. 19B, however, the heart rhythms 500-2 of FIG. 20B have inter beat interval values that frequently span across 3 standard deviations above and below the average, and are much more erratic in period and signal shape.

Figures 21A, 21B:
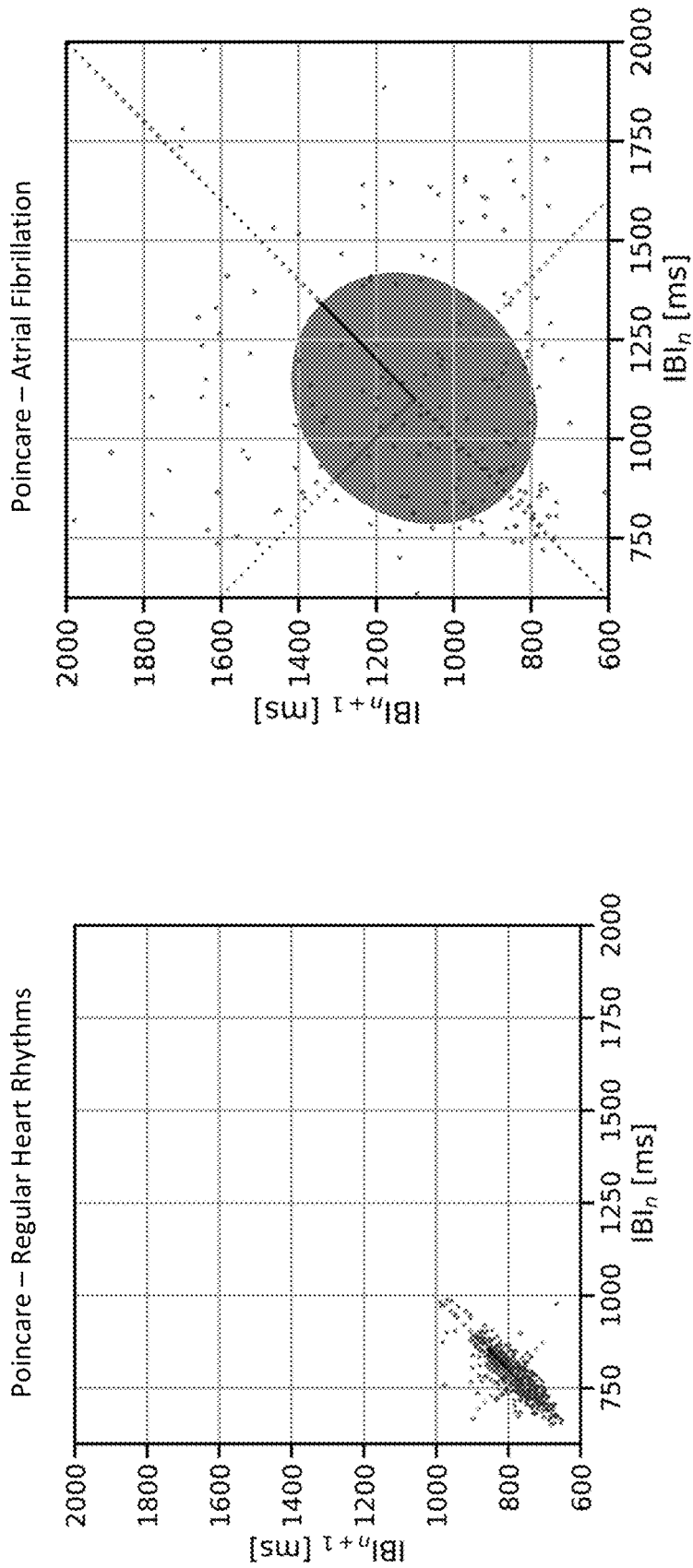
FIGS. 21A and 21B are, respectively, Poincare plots of inter beat intervals from the heart rhythm plots of the healthy individual in FIG. 19B and the unhealthy individual in FIG. 20B.

FIGS. 21A and 21B illustrate how the analysis module 180 can also determine the heart rhythm 500-1 of the individuals 100 using Poincare distributions of the inter beat intervals. FIG. 21A shows a Poincare distribution of the inter beat intervals 320 for the pulse wave signals 301 of the healthy individual 100 in FIG. 19A, while FIG. 21B shows a Poincare distribution that plots changes in the inter beat intervals 320 over time for the pulse wave signals 301 of the individual 100 experiencing Afib in FIG. 20A.

In FIG. 21A, the Poincare distribution of the healthy individual is obtained by plotting inter beat intervals 320 versus n+1 inter beat intervals. The distribution is further used to quantify features. The primary features from the Poincare distribution or diagram can be based on parameterization as e.g., an ellipse and parameters derived from the ellipse, including standard deviations along major and minor axes, their ratio, and the area of the ellipse. Alternatively, the Poincare diagram can be converted to an image. The data analysis system 209 can then execute image processing and analysis algorithms upon the image to classify between sinus rhythms and heart arrhythmias.

In FIG. 21B, a Poincare distribution of an individual 100 with diagnosed Afib is shown. The Afib condition was detected by the cardiology system 10. The scatter of the inter beat intervals is characteristic of the irregular rhythms of Afib and is well detected by the cardiology system 10.

Figure 22A:
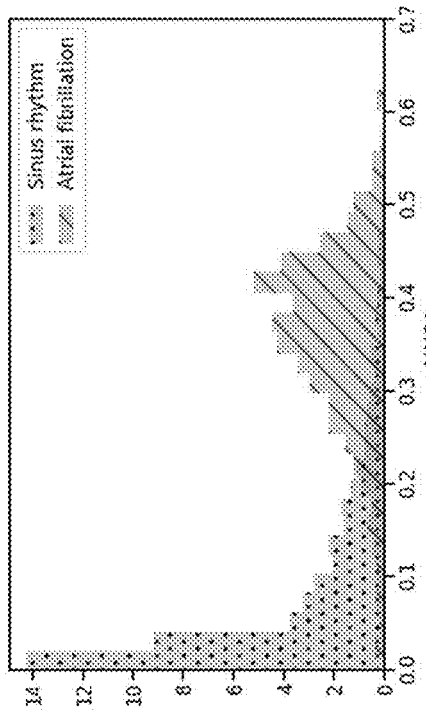
FIG. 22A-D show plots of exemplary features for regular and Afib heart rhythms over time, where the plots demonstrate clear separation between regular and Afib heart rhythms, and where.
Figure 22B:
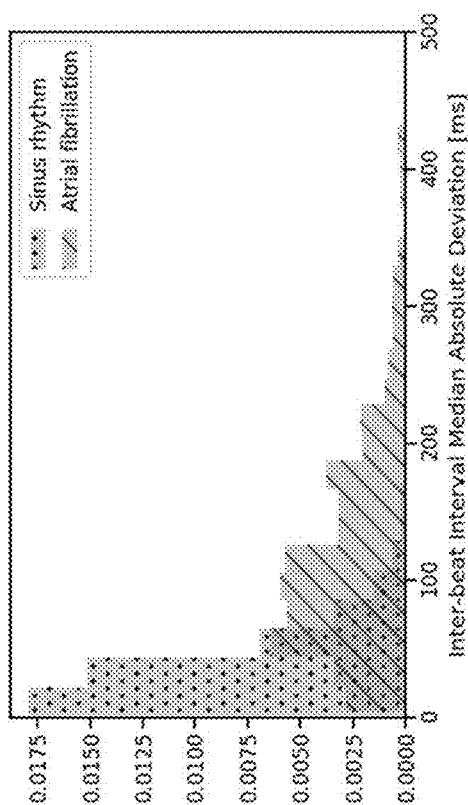
Figure 22C:
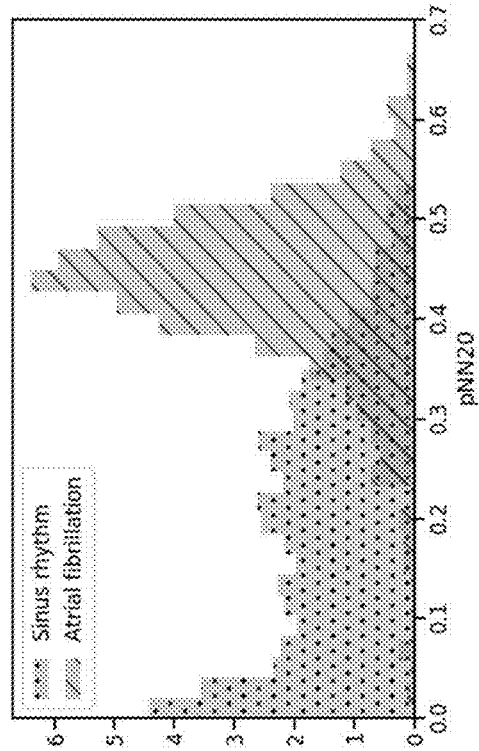
Figure 22D:
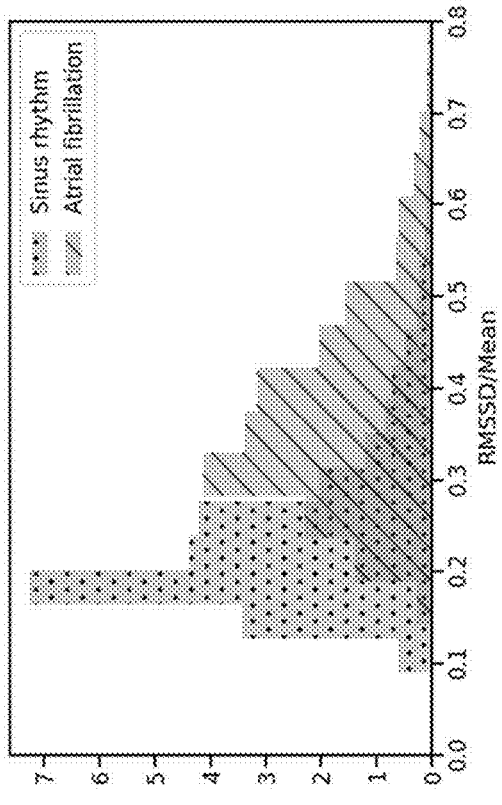

FIGS. 22A-D show distributions of exemplary features for regular and Afib heart rhythms. The figures demonstrate clear separation between regular and Afib heart rhythms. Such distributions can be created from training data sets in combination with real-time data from the individual 100. In more detail, FIG. 22A uses an inter beat interval median absolute deviation statistic. FIG. 22B uses a pNN50 heart rate variability statistic. FIG. 22C uses an RMSSD/Mean statistic. FIG. 22D uses a pNN20 heart rate variability statistic. The terms pNN20/pNN50 are fractions of successive inter-beat interval differences exceeding 20 ms/50 ms within a signal segment, respectively.

Returning to the method of FIG. 12, in step 218, the analysis module 180 can classify the heart rhythms 500. In one example, the analysis module 180 classifies the heart rhythms 500 using machine learning (ML) algorithms based upon information derived from the biosignals 101, where the information includes features calculated from inter beat intervals and their distributions, the stroke volume, and possibly the pulse wave shape. In another example, either the pulse wave signals 301, or the information derived from the pulse wave signals 301 can be passed to the machine learning module 182. Using training data, the machine learning module 182 might classify the heart rhythms 500. The training data typically include both datasets of biosignals 101 and publicly available ECG datasets.

The machine learning module 182 for distinguishing between heart arrhythmias typically takes two primary forms. In one form, classification algorithms such as tree-based classifiers (e.g., random forest, boosted decision tree models), support vector machines, and neural networks are applied to features calculated from pulse wave signals described above. In another example, the machine learning module involves deep learning algorithms, such as deep neural networks, convolutional neural networks, and recurrent neural networks trained on the pulse wave signals 301 or simple transformations of the pulse wave signals 301 such as a periodogram or a spectrogram. As a result, in one implementation, the data analysis system 209 determines arrhythmias including atrial fibrillation (Afib) arrhythmias by detecting pulse wave signals 301 in the biosignals 101 and characterizing the overall pulse wave signal shape and changes in the pulse wave signal shape over time.

The data analysis system 209 can also determine the heart rhythms 500 of the individual 100 without monitoring the pulse sites of the individual.

Also in step 218, the data analysis system 209 can determine arrhythmias including atrial fibrillation (Afib) arrhythmias from the heart rhythms. For this purpose, the analysis module 180 and/or machine learning module 182 classifies the heart rhythm as being regular in nature (sinus rhythm), or irregular in nature (unhealthy arrhythmia). As a result, the analysis module 180 can distinguish the atrial fibrillation arrhythmias from regular rhythms and other arrhythmias.

For the sinus rhythm case detected in step 218, the regular nature/waveform may still be indicative of an arrhythmia, though such an arrhythmia is generally not as serious as in the irregular rhythm case. When a sinus rhythm is detected, the method transitions to step 222, and the analysis module 180 examines the heart speed and stroke volume 210 to determine the type of arrhythmia (normal sinus/no arrhythmia, tachycardia, or bradycardia). According to step 222, the analysis module 180 classifies the heart rhythms 500 into the three classes of arrhythmias (e.g. bradycardia, tachycardia and normal sinus/extra heartbeats).

When no arrhythmia/extra heartbeats is detected in step 222, indicated by path A, the heart rhythm is generally considered to be normal. However, when extra heartbeats are detected, the method distinguishes the premature atrial complexes (PACs) from the premature ventricular contractions (PVCs), and can additionally guage whether these typically infrequent extra or skipped beats are a new phenomenon for the individual 100, or have changed/become worse. For this purpose, the method can compare the detected extra beats and/or their stroke volumes 210 against those of the stored baseline heart rhythm 920 for the individual 100, determine whether the extra beats are persistent over a period of minutes or hours (rather than random or infrequent), or detemine whether the extra beats have increased beyond a threshold value, in examples. In these cases, the method would notify the individual 100 and/or the health and safety professionals 110 of the condition. Upon complettion of step 222, the method transitions to step 250.

In step 250, the analysis module 180 sends a message such as a notification message 111 to update the stored medical record 50 for the individual 100 with the results of the analysis. Upon completion of step 250, the method transitions back to step 208 to receive new biosignals 101 from the earbuds 103L, 103R.

When a tachycardia arrhythmia is detected in step 222, indicated by path B, the method distinguishes the supraventricular tachycardias (SVT) from the ventricular tachycardias (VT) and then transitions to step 228. In step 228, the analysis module 180 might send a message such as a notification message 111 to the user app 40. The message might include information (audible and/or visual) recommending that the individual 100 perform breathing exercises in an attempt to slow down the heart rate. The user app 40 may also forward the information to the earbuds 103L, 103R for possible audio presentation at the earbuds 103L, 103R. The method then transitions to step 250.

When a bradycardia arrhythmia is detected in step 222, indicated by path C, the method transitions to step 224. In step 224, the analysis module 180 determines whether the heart speed and/or stroke volume of the detected heart rhythm is normal as compared to the heart speed and/or stroke volume of the stored baseline heart rhythm 920 in the medical record 50 of the individual 100. For this purpose, in one example, specific criteria (e.g. amplitude, speed) between the current and stored heart rhythms can be compared. A rank value that indicates how closely each specific criteria matches is then calculated, and summed to form a score. Scores meeting a threshold score value would be considered as "normal." If the comparison is normal, the method transitions to step 250. Otherwise, the method transitions to step 226.

In step 226, the analysis module 180 sends a warning message to the individual 100. In one example, the message tells the individual 100 to check their pacemaker. The method then transitions to step 250.

For the irregular rhythm (unhealthy arrhythmias) case detected in step 218, the method transitions to step 230. In step 230, the analysis module 180 assesses a type and sets a "notify doctor" flag based on user conditions associated with each type.

Figure 23:
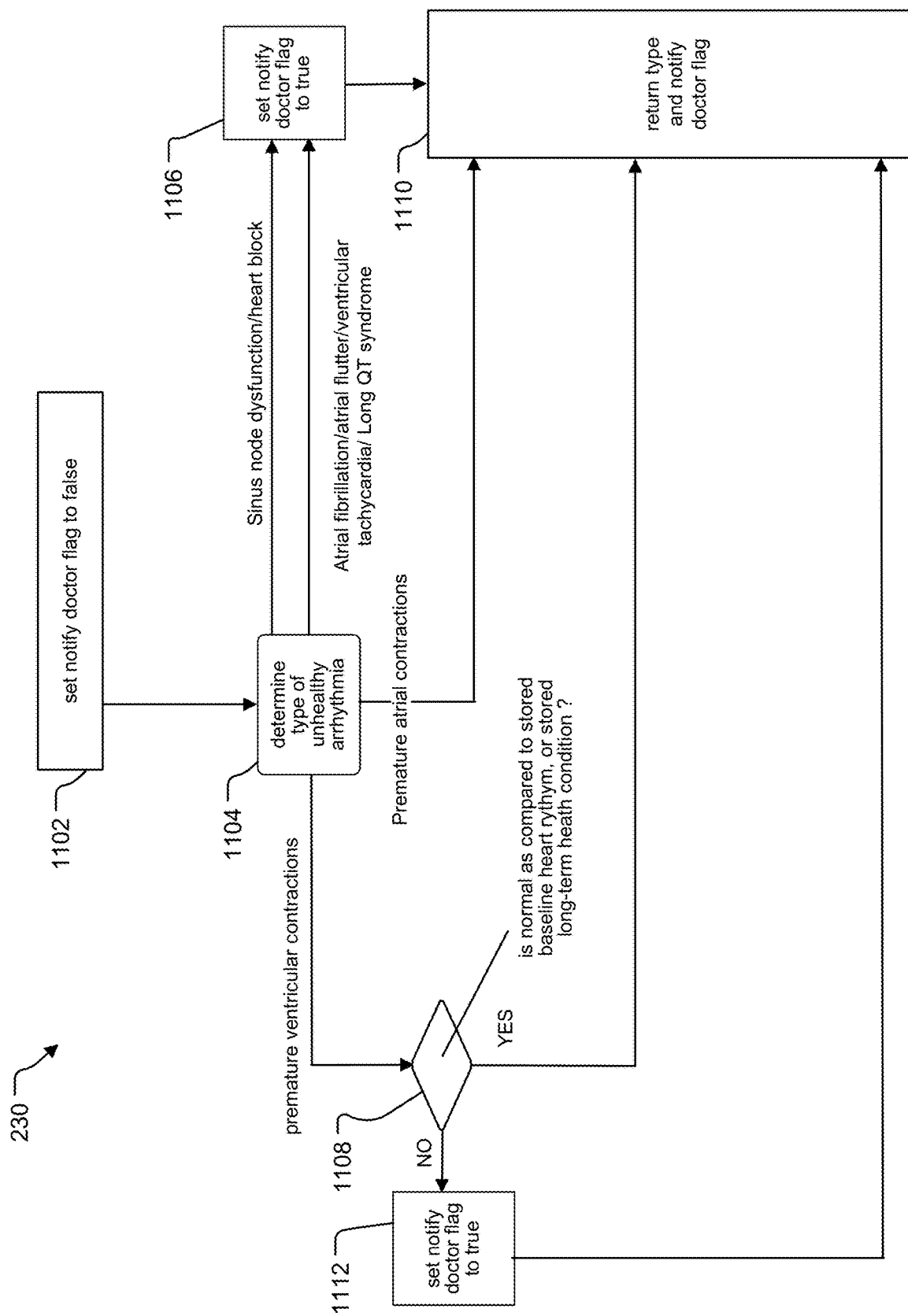
FIG. 23 is a flow chart that shows more detail for notification and reporting features within the method of FIG. 12.

FIG. 23 shows more detail for FIG. 12 step 230.

In step 1102-1, the analysis module 180 sets the 'notify doctor flag' to false. In step 1104, the analysis module 180 determines the type of unhealthy arrhythmia from the heart rhythms. The types include: premature ventricular contractions, sinus node dysfunction/heart block, atrial fibrillation (Afib)/atrial flutter/ventricular tachycardia/long QT syndrome, and premature atrial contractions, in examples.

When the unhealthy arrhythmia is PVCs, the method transitions to step 1108. Here, the analysis module 18 determines if the contractions are normal as compared to stored baseline heart rhythm 920, or other stored long-term health conditions. If the contractions are not normal, the method transitions to step 1112, and sets the 'notify doctor flag' to true. The method then transitions to step 1110. If the contractions are normal, the method transitions to step 1110.

When the unhealthy arrhythmia is either sinus node dysfunction/heart block or atrial fibrillation (Afib)/atrial flutter/ventricular tachycardia/long QT syndrome, the method transitions to step 1106. Here, the analysis module 180 sets the 'notify doctor flag' to true, and the method then transitions to step 1110. When the unhealthy arrhythmia is PACs, the method transitions to step 1110. In step 1110, the method returns the unhealthy arrhythmia type and the state of the 'notify doctor flag.'

Returning to the method of FIG. 12, upon completion of step 230, the method transitions to step 232. In step 232, the analysis module 180 determines whether the unhealthy arrhythmia persists for more than 2-3 minutes or is accompanied by fainting, shortness of breath or chest pain. If either of these conditions are met, the method transitions to step 236, and the analysis module 180 sends a message to the user app 40 to call the first responders 99 and/or the health care and safety professionals 110. The method then transitions to step 250. Otherwise, if these conditions are not met, the method transitions to step 234.

In step 234, the analysis module 180 determines whether the 'notify doctor flag' is set to true. If the flag is set to true, the method transitions to steps 236 and 250. Otherwise, the method transitions to step 238.

In step 238, the individual 100 has a known unhealthy arrhythmia that has not significantly changed as compared to the baseline heart rhythm in their medical record 50. As a result, there is likely no need to treat the arrhythmia. Thus, there is no need to report the detected/classified arrhythmia to the health care and safety professionals 110 or notify the first responders 99. At the same time, the analysis module 180 sends a message 111 to the user app 40 suggesting that the individual 100 perform meditation, yoga, or other relaxation techniques.

When sending messages, the data analysis system 209/ analysis module 180 sends the notification messages 111 via the application server 132 and wireless link 66-2 to the user app 40 on the user device 107-1A. Depending on the type of message, the user app 40 may present a visual message for display upon its GUI, play an audio message at a speaker of the user device 107-1A, or possibly even forward an audio message directly over wireless link 66-1 to the controller board 105 for audio presentation at speakers within one or more of the earbuds 103L, 103R.

During the analysis, in one example, the analysis system 209 might detect a low signal amplitude of the biosignals 101. This is usually due to a poor earbud fit/seal within the ear of the individual 100. Via the application server 132 and the wireless connection 66-1, the analysis system 209 can send a text message to the user device 107-1 instructing the individual 100 to adjust the fit of the earbuds to form a tighter seal. The user device 107-1 might also send the message for presentation at a display 88 of a bionic contact lens 123 worn by the user.

After the analysis, in another example, the analysis system 209 might send an audio message to the earbuds 103L, 103R upon detecting a fast heartbeat (tachycardia) arrhythmia. The message instructs the individual 100 to perform relaxation techniques such as meditation or yoga. Via the application server 132 and the wireless connections 66-1 and 66-2, the analysis system 209 sends the message to the controller board 105. The controller board 105 then transmits the message to the speakers of the earbuds 103L, 103R.

While this invention has been particularly shown and described with references to preferred embodiments thereof, it will be understood by those skilled in the art that various changes in form and details may be made therein without departing from the scope of the invention encompassed by the appended claims.

What is claimed is:

1. A cardiology system for detecting and analyzing heart rhythms, the system comprising:
   a biosensor system configured to be worn by an individual, wherein the biosensor system includes sensors that detect biosignals including infrasonic signals from the individual; and
   a data analysis system that receives the biosignals from the biosensor system, and determines heart rhythms of the individual based upon the biosignals;
   wherein the biosensor system is an in-ear biosensor system that includes at least one earbud, and wherein the at least one earbud includes the sensors that detect the biosignals including infrasonic signals; and
   wherein the data analysis system is configured to use the biosignals and/or the heart rhythms to identify a condition of the individual.

2. The system of claim 1, further comprising an auxiliary sensor for detecting pressure biosignals in the individual's ear to monitor occlusion level of the at least one earbud and to monitor physiological changes of the individual.

3. The system of claim 1, wherein the in-ear biosensor system detects biosignals from left and right earbuds for improving a signal to noise ratio of the biosignals.

4. The system of claim 1, wherein the data analysis system determines heart rhythms of the individual based upon the biosignals by detecting pulse wave signals in the biosignals, determining inter beat intervals of the heart based upon the pulse wave signals, and computing the heart rhythms from the inter beat intervals.

5. The system of claim 1, wherein the data analysis system determines heart rhythms of the individual based upon the biosignals by detecting pulse wave signals in the biosignals, calculating stroke volumes under each of the pulse wave signals during systole times, and computing the heart rhythms from changes in the stroke volumes.

6. The system of claim 1, wherein the condition identified by the data analysis system includes arrhythmias including atrial fibrillation (Afib) arrhythmias, and wherein the data analysis system determines the arrhythmias by detecting pulse wave signals in the biosignals and characterizing the overall pulse wave signal shape and changes in the pulse wave signal shape over time.

7. The system of claim 1, wherein the condition identified by the data analysis system includes arrhythmias including atrial fibrillation (Afib) arrhythmias, and wherein the data analysis system determines the arrhythmias from the heart rhythms.

8. The system of claim 1, wherein the data analysis system identifies and removes motion artifacts associated with motion of the individual from the biosignals prior to determining the heart rhythms of the individual.

9. The system of claim 1, wherein the data analysis system identifies and distinguishes premature ventricular contractions (PVCs) conditions from premature atrial complexes (PACs) conditions and identifies and distinguishes supraventricular tachycardias (SVT) conditions from ventricular tachycardias (VT) conditions.

10. The system of claim 1, further comprising at least one user device including a cardiovascular user application (user app) executing upon a CPU of the user device, wherein the user app communicates with the biosensor system to control the sending of the biosignals to the data analysis system.

11. The system of claim 1, wherein the data analysis system is distributed across one or more computer nodes in a remote network.

12. The system of claim 1, wherein the data analysis system is included within one or more user devices.

13. The system of claim 1, wherein the data analysis system is included within the biosensor system.

14. The system of claim 1, wherein the data analysis system is distributed across a user device and at least one computer node of a remote network.

15. The system of claim 1, wherein the data analysis system notifies the individual and other persons regarding the condition.

16. The system of claim 1, wherein when the condition is an unhealthy arrhythmia that the data analysis system determines does not require treatment, the data analysis system notifies the individual to perform relaxation techniques in response.

17. A method for detecting and analyzing heart rhythms, the method comprising:
   detecting biosignals including infrasonic signals from the individual via sensors of a biosensor system worn by the individual, wherein the biosensor system is an in-ear biosensor system including at least one earbud;
   determining heart rhythms of the individual based upon the biosignals; and
   using the biosignals and/or the heart rhythms to identify a condition of the individual.

18. The method of claim 17, wherein determining heart rhythms of the individual based upon the biosignals comprises:

detecting pulse wave signals within the biosignals and calculating inter beat intervals from the pulse wave signals; and computing the heart rhythms from the inter beat intervals.

19. The method of claim 17, wherein determining heart rhythms of the individual based upon the biosignals comprises:

detecting pulse wave signals within the biosignals and calculating stroke volumes under each of the pulse wave signals during systole times; and computing the heart rhythms from changes in the stroke volumes.

20. The method of claim 17, wherein using the biosignals and/or the heart rhythms to identify a condition of the individual comprises determining arrhythmias including atrial fibrillation (Afib) arrhythmias by detecting pulse wave signals in the biosignals and characterizing the overall pulse wave signal shape and changes in the pulse wave signal shape over time.

21. The method of claim 17, wherein using the biosignals and/or the heart rhythms to identify a condition of the individual comprises identifying arrhythmias including atrial fibrillation (Afib) arrhythmias from the heart rhythms.

22. The method of claim 17, wherein determining heart rhythms of the individual based upon the biosignals is accomplished at the level of the biosensor system.

23. The method of claim 17, further comprising detecting a pressure in the individual's ear to monitor an occlusion level of the at least one earbud and to monitor physiological changes of the individual, via an auxiliary sensor.

24. The method of claim 17, further comprising detecting biosignals from left and right earbuds for improving a signal to noise ratio of the biosignals.

25. The method of claim 17, further comprising identifying and removing motion artifacts associated with motion of the individual from the biosignals prior to determining the heart rhythms of the individual.

26. The method of claim 17, further comprising identifying and distinguishing premature ventricular contractions (PVCs) conditions from premature atrial complexes (PACs) conditions and identifying and distinguishing supraventricular tachycardias (SVT) conditions from ventricular tachycardias (VT) conditions.

27. The method of claim 17, wherein determining heart rhythms of the individual based upon the biosignals is accomplished at a user device.

28. The method of claim 17, wherein determining heart rhythms of the individual based upon the biosignals comprises processing the heart rhythms at a user device and at least one computer node of a remote network.

29. The method of claim 17, further comprising updating a medical record of the individual in response to determining the heart rhythms of the individual.

30. The method of claim 17, further comprising notifying health care and safety professionals in response to determining the heart rhythms of the individual.

31. The method of claim 17, further comprising notifying the individual and other persons regarding the condition.

* * * * *